US011021505B2

(12) United States Patent
Oger et al.

(10) Patent No.: US 11,021,505 B2
(45) Date of Patent: Jun. 1, 2021

(54) AQUEOUS EXTRACT ENRICHED WITH SMALL RNAS AND COMPOSITIONS COMPRISING SUCH EXTRACTS AND TO THEIR COSMETIC USES

(71) Applicant: ISP INVESTMENTS LLC, Wilmington, DE (US)

(72) Inventors: Elodie Oger, Vallauris (FR); Valerie Lequoy, Valbonne (FR); Frederique Portolan, Valbonne (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 349 days.

(21) Appl. No.: 15/774,754

(22) PCT Filed: Nov. 10, 2016

(86) PCT No.: PCT/EP2016/077231
§ 371 (c)(1),
(2) Date: May 9, 2018

(87) PCT Pub. No.: WO2017/084958
PCT Pub. Date: May 26, 2017

(65) Prior Publication Data
US 2018/0371000 A1 Dec. 27, 2018

(30) Foreign Application Priority Data

Nov. 17, 2015 (FR) ...................... 1502361

(51) Int. Cl.
| | |
|---|---|
| *C12N 15/10* | (2006.01) |
| *C07H 1/08* | (2006.01) |
| *A61K 8/60* | (2006.01) |
| *C07H 21/02* | (2006.01) |
| *A61Q 19/08* | (2006.01) |
| *A61K 8/9789* | (2017.01) |
| *A61Q 19/00* | (2006.01) |
| *A61Q 17/04* | (2006.01) |
| *A61K 8/9794* | (2017.01) |
| *A61K 8/44* | (2006.01) |

(52) U.S. Cl.
CPC ................ *C07H 1/08* (2013.01); *A61K 8/44* (2013.01); *A61K 8/606* (2013.01); *A61K 8/9789* (2017.08); *A61K 8/9794* (2017.08); *A61Q 17/04* (2013.01); *A61Q 19/00* (2013.01); *A61Q 19/007* (2013.01); *A61Q 19/08* (2013.01); *C07H 21/02* (2013.01); *C12N 15/1003* (2013.01); *C12N 15/1017* (2013.01); *A61K 2800/10* (2013.01); *A61K 2800/30* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 7,211,269 B2 | 5/2007 | Dal Farra et al. | |
| 7,396,815 B2 | 7/2008 | Dal Farra et al. | |
| 2003/0092168 A1* | 5/2003 | Lubrano ............ | C12N 15/1003 435/270 |
| 2012/0220541 A1 | 8/2012 | Dal Farra et al. | |

FOREIGN PATENT DOCUMENTS

| | | |
|---|---|---|
| CN | 101601635 A | 12/2009 |
| DE | 19820629 A1 | 11/1999 |
| EP | 1723958 * | 11/2006 |
| EP | 1723958 A2 | 11/2006 |
| FR | 2817748 A1 | 6/2002 |
| FR | 2827170 A1 | 1/2003 |
| FR | 2831168 A1 | 4/2003 |
| FR | 2837098 A1 | 9/2003 |
| FR | 2841781 A1 | 1/2004 |
| FR | 2846883 A1 | 5/2004 |
| FR | 2912313 A1 | 8/2008 |
| FR | 2940112 A1 | 6/2010 |
| FR | 2944526 A1 | 10/2010 |
| FR | 2951946 A1 | 5/2011 |
| FR | 2956818 A1 | 9/2011 |
| WO | 84/03835 A1 | 10/1984 |
| WO | 02/057289 A1 | 7/2002 |
| WO | 03/101376 A2 | 12/2003 |
| WO | WO 03/101376 * | 12/2003 |
| WO | WO 03/101376 A2 * | 12/2003 |
| WO | 2004/046305 A2 | 6/2004 |
| WO | 2005/034648 A2 | 4/2005 |

OTHER PUBLICATIONS

PCT, International Search Report (with English translation), International Application No. PCT/EP2016/077231, 9 pages, Feb. 1, 2017.
DePaulo, J.J. et al., "Extraction of Double-Stranded Rna from Plant Tissues Without the Use of Organic Solvents," Plant Disease, vol. 79, No. 3, pp. 246-248, Mar. 1995.
Dos Reis Falcao, V. et al., RNA Isolation method for polysaccharide rich algae: agar producing *Gracilaria tenuistipitata* (Rhodophyta), J. Appl. Phycol., vol. 20, No. 1, pp. 9-12, 2008.
Zhang, P. et al., "Use of small RNA as antiaging cosmeceuticals," J. Cosmet. Sci., pp. 455-468, Nov./Dec. 2013.
Zumbo, P., "Phenol-chloroform Extraction," 7 pages, 2014.

* cited by examiner

*Primary Examiner* — Ralph J Gitomer
(74) *Attorney, Agent, or Firm* — Thompson Hine LLP

(57) ABSTRACT

The invention relates to an aqueous extract enriched with small RNA having a maximum length of 150 nucleotides, from plant material. The invention relates to an aqueous extract of plant material, enriched with small RNAs having a maximum length of 150 nucleotides, which can be obtained by such a method, as well as to the compositions comprising such an extract and to their cosmetic uses for combating the signs of skin aging and for improving the hydration of the skin.

5 Claims, 2 Drawing Sheets

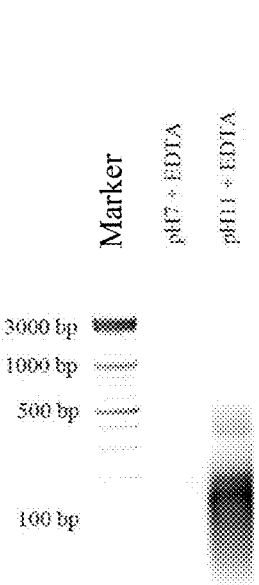
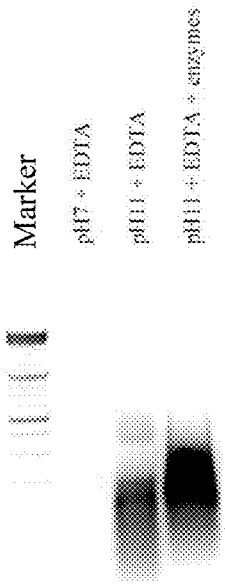

FIG. 1A: electrophoresis on 2% agarose gel showing the effect of the pH on the extraction of the RNA of rice germ

FIG. 1B: electrophoresis on 2% agarose gel showing the effect of the enzymatic hydrolysis on the extraction of the RNA of rice germ

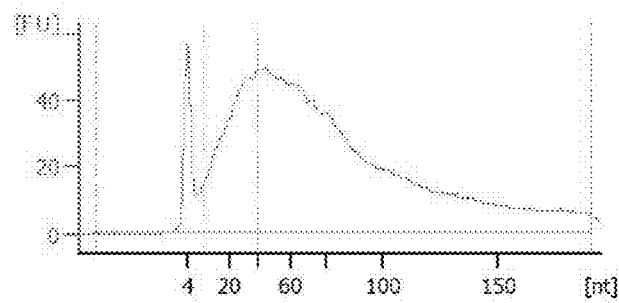

FIG. 2: quantification of the low molecular weight RNA in the extract of lentils by Bioanalyseur®

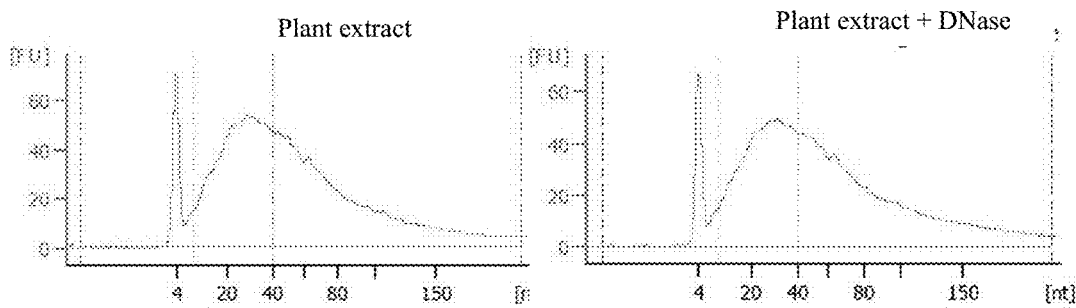

FIG. 3: quantification of the low molecular weight RNA by Bioanalyseur® (in the treated or untreated plant extract)

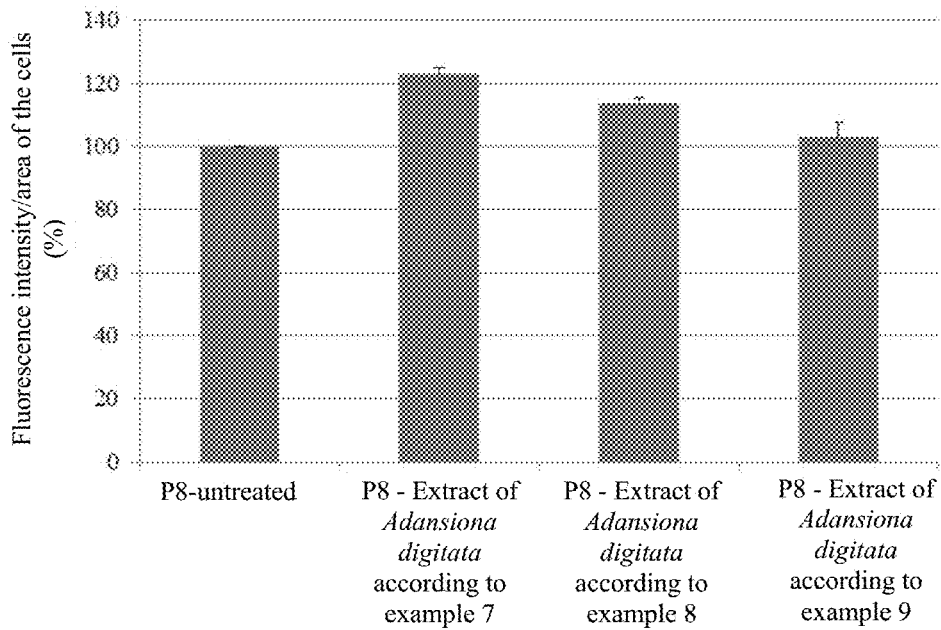
FIG. 4A: quantification of the expression of HAS2 by immunofluorescence in fibroblasts (passage 8) after a 48h treatment with the different extracts
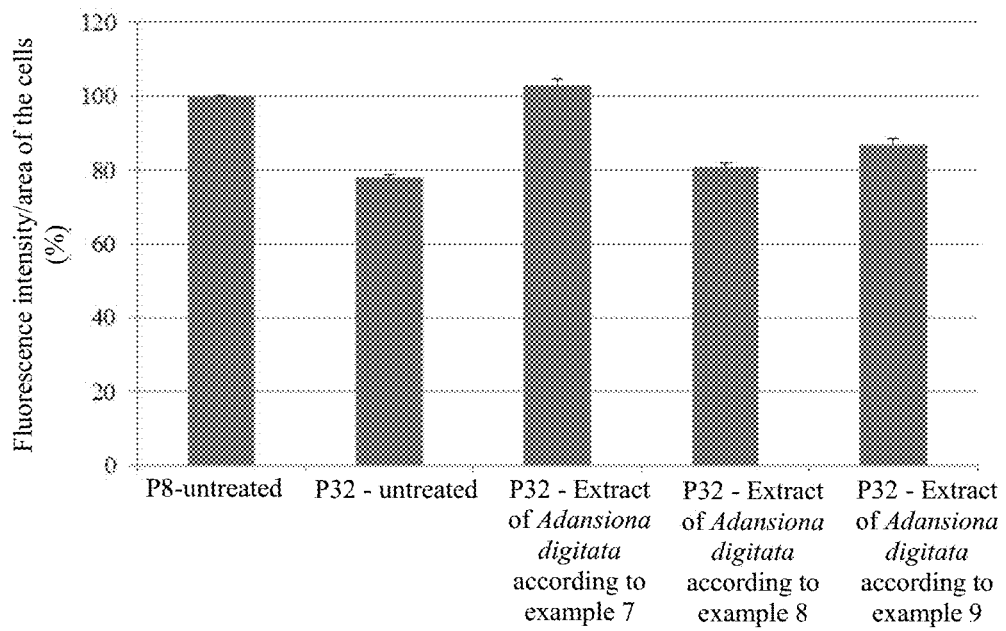
FIG. 4B: quantification of the expression of HAS2 by immunofluorescence in fibroblasts (passage 32) after a 48h treatment with the different extracts

AQUEOUS EXTRACT ENRICHED WITH SMALL RNAS AND COMPOSITIONS COMPRISING SUCH EXTRACTS AND TO THEIR COSMETIC USES

The invention relates to a method for obtaining an aqueous extract enriched with small RNA (ribonucleic acids) having a maximum length of 150 nucleotides (nt), from plant material to the extracts originating from such a method, as well as to the compositions comprising such extracts and to their cosmetic uses.

The conventional protocols for extraction of ribonucleic acids (RNA, low molecular weight RNA) carried out in the laboratory and thus on a small scale have to take place under a chemical hood, since these processes involve the use of solvents such as phenol and chloroform which are toxic and not considered cosmetic solvents (lumbo, P. 2014 "Phenol-chloroform Extraction," 2014). These solvents are added to an aqueous phase of lysed cells or of very finely crushed plant or animal tissues, or directly to the crushed preparation produced in the presence of liquid nitrogen. The solution thus obtained is centrifuged at high speed on the order of 10,000 g at 4° C. so as to create two well separated phases, an organic phase which contains the proteins and an aqueous phase which contains the total RNA, the intermediate phase containing the DNA. The aqueous phase then has to be carefully recovered so as not to inadvertently collect the intermediate and organic phase. A step of precipitation of the RNA is carried out with isopropanol. The total RNA pellet is then washed with ethanol. The total RNA is then resolubilized in water and has to be stored at very low temperature (−20° C. and even better −80° C.)

In order to obtain only the low molecular weight RNA, it is possible to use kits containing purification columns, such as the kit from Sigma, the mirPremier™ microRNA Isolation Kit. These kits can only be used on the laboratory test scale, since the volumes in question are on the order of a mL and can therefore not be adapted to product development on a large scale.

In addition, all these extraction and purification protocols will not make it possible to obtain the purified nucleic acid fraction. This RNA or DNA or small RNA nucleic acid fraction will be free of any other molecule of interest such as secondary metabolites, vitamins, sugars, peptides, etc., which can have beneficial effects for the skin and thus be of cosmetic interest.

Moreover, for example, document WO8403835 is known, which describes a method for obtaining an aqueous extract of plant embryos enriched with pure DNA. Such a method uses notably wheat embryos and/or soybean embryos crushed in a buffered extraction solution at pH 9.5 containing sucrose, EDTA (0.05 M) and sodium chloride. After filtration, the residue is resuspended in a buffered saline Tris solution at pH 7.4 supplemented with anionic detergent under stirring at ambient temperature, followed by the addition of sodium perchlorate under stirring at 0° C., and the addition of chloroform and octanol before centrifugation at low temperature (4° C.) and at very high speed (25,000 g). An aqueous phase containing essentially DNA with a small quantity of RNA and of amino acids is recovered, on which an RNase can advantageously be made to act.

This document thus discloses the obtention of an aqueous extract of plant embryos enriched specifically with DNA using a very large number of treatments, including treatments with an anionic detergent and different solvents, including chloroform and octanol which can leave toxic traces in the products and can thus not be used in cosmetics.

The document FR2831168 is also known, which describes a method for obtaining an extract rich in nucleic acids (DNA and/or RNA) from plant material, in particular plant embryos or seeds with high DNA or RNA content. The method consists in extracting, in an aqueous medium, plant material in the presence of cellulolytic enzymes at an initial pH from 9 to 13, the pH evolving towards neutrality (optimal pH for the action of these enzymes) within a few minutes, then separating the plant material in order to recover an aqueous extract, and finally treating the extract with a protease and separating the insoluble substances in order to recover a purified aqueous extract. The lyophilized product thus obtained can contain, in particular, from 0.1 to 1% by weight of DNA, from 0.2 to 1.5% by weight of RNA, as well as carbohydrates, proteins, minerals, vitamin B and lipids.

In particular, based on the data described in this document, the lyophilized product obtained thus appears to contain from 1 to 10 mg/L of DNA and from 10 to 75 mg/L of RNA.

Considering the above, a problem which the invention proposes to resolve is to develop a method for obtaining an aqueous extract enriched specifically with small RNA and comprising no DNA, from plant material, which is easy and inexpensive to carry out on the industrial scale, does not obligatorily require the use of cellulolytic enzymes (cellulase, hemicellulase) or of DNase, offers good yields of small RNA, and does not have the disadvantages of the methods of the mentioned prior art such as, for example, the use of detergent and potentially toxic solvents.

The extract thus obtained can then be used directly in cosmetics.

The first subject matter of the invention thus is a method for obtaining an aqueous extract enriched with small RNA having a maximum length of 150 nucleotides, from plant material, comprising the following steps:

a) the plant material is put in contact with water;

b) tetrasodium ethylenediaminetetraacetic acid (EDTA) is added to a mixture obtained in a), the pH of the mixture being between 10.5 and 11;

c) then, the pH of the mixture obtained in b) is adjusted to a value between 6 and 8;

d) the mixture obtained in c) is purified in such a manner as to eliminate the plant material and to recover an aqueous raw extract; and e) at least one filtration of the aqueous raw extract is carried out in order to obtain the aqueous extract enriched with small RNA having a maximum length of 150 nucleotides, the pH of which is checked and if necessary adjusted to a value between 6 and 8, preferably between 6 and 6.5.

In addition, the second subject matter of the invention is an aqueous extract of plant material, enriched with small RNA having a maximum length of 150 nucleotides, obtained by the method according to the invention, wherein it comprises, by weight relative to the total weight of the extract, 5 to 60 g/kg of dry extract and 10 to 1000 mg/kg of small RNA having a maximum length of 150 nucleotides and comprises no DNA.

The third subject matter of the invention is a composition comprising an effective quantity of an extract according to the invention, as anti-aging active agent, and a physiologically acceptable medium.

The fourth subject matter of the invention is the cosmetic use of a composition according to the invention for combating the signs of skin aging.

Finally, the fifth subject matter of the invention is the cosmetic use of a composition according to the invention for improving the hydration of the skin.

The invention and the advantages derived therefrom will be understood better upon reading the description and the following non-limiting embodiments, drafted in reference to the appended figures in which:

FIG. 1A represents an electrophoresis on agarose gel at 2% demonstrating the effect of the pH on the extraction of low molecular weight RNA in extracts according to example 2 (rice germ) of the invention;

FIG. 1B represents an electrophoresis on agarose gel at 2% demonstrating the effect of an enzymatic hydrolysis on the extraction of low molecular weight RNA in extracts according to example 2 (rice germ) of the invention;

FIG. 2 represents the quantification with the Bioanalyseur® of the low molecular weight RNA of an extract according to example 3 (lentils) of the invention;

FIG. 3 represents the quantification with the Bioanalyseur® of the low molecular weight RNA of the extract according to example 4 (lentils) of the invention, before and after treatment with the DNase;

FIG. 4A represents the effect of different extracts of baobab (*Adansiona digitata*) according to examples 7, 8 and 9 on the expression of the hyaluronane synthase 2 (HAS2) on passage 8 (P8) human fibroblasts and FIG. 4B represents the effect of different extracts of baobab (*Adansiona digitata*) according to examples 7, 8 and 9 on the expression of the hyaluronane synthase 2 (HAS2) on passage 32 (P32) human fibroblasts.

Unless otherwise indicated, in this description, it is understood that, when an interval is given, it includes the upper and lower limits of said interval.

The invention relates to a method implemented for obtaining an aqueous extract enriched with small RNA having a maximum length of 150 nucleotides, from plant material. It should be noted that the method of the invention can be preceded by any type of preliminary extraction step known to the person skilled in the art (chemical hydrolysis, enzymatic hydrolysis . . . ), making it possible, for example, to eliminate beforehand certain plant fractions which could be detrimental to the proper running of the method of the invention.

"Small RNA" or "low molecular weight RNA" is understood to mean non-coding RNA (ribonucleic acids) having a low molecular weight, and having a maximum length of 150 nucleotides, such as all the single stranded and/or double stranded non-messenger small RNA types, for example, micro RNA, interfering RNA, the introns, small nuclear RNA or any RNA fragment.

In general, plant material is a plant, a living organism which is part of the plant kingdom, characterized by a very low motility, which feeds on mineral substances and absorbs carbon dioxide, including plants whose life cycle generally takes place in an aquatic environment, such as algae.

Advantageously, for the implementation of the method, the plant material according to the invention is a whole plant or preferably a plant part (fruit, leaves, roots, bulbs, germs, seeds . . . ), which can be used in fresh, dry, germinated, whole, powdered, frozen form, but also in the form of a plant residue obtained after transformation such as oilcakes or spent grain. To achieve this, all the parts of the mentioned plant species can be used to obtain an extract, an aqueous extract enriched with small RNA having a maximum length of 150 nucleotides. Thus, the examples concerning certain parts of the plant are given for illustration and in a non-limiting manner.

Advantageously, one can consider using any fruit or fruit part as starting plant material for obtaining an aqueous extract enriched with low molecular weight RNA. For example, one can mention the whole fruits, fruits in the form of pieces, in the form of a powder, fresh or frozen, in the form of spent grain. One can mention the fruits of the family of the Passifloraceae, but also fruits of other families such as fruits of the family of the Malvaceae, such as *Hibiscus esculentus* (okra). One can also mention fruits of the family of the Punicaceae such as *Punica granatum* (pomegranate), the fruits of the family of the Actinidiaceae such as *Actinidia chinensis* (kiwi fruit), of the family of the Myrtaceae such as *Psidum guajava* (guava), the fruits of the family of the Clusiaceae such as *Garcinia cambodgia* (Malabar tamarind), the family of the Caricaceae such as *Carica papaya* (*papaya*). One can also consider using fruits belonging to the family of the Malphigiaceae such as *Malphigia glabra* (acerola), the fruits in the form of berries such as the fruits of the family of the Ericaceae such as *Vaccinium myrtillus* (whortleberry) and of the family of the Grossulariaceae such as *Ribes nigrum* (blackcurrant). Or any fruit of the family of the Solanaceae, such as *Lycium barbarum* (wolfberry) can be considered.

An aqueous extract enriched with low molecular weight RNA can also be obtained from any flower in whole form, in the form of a powder, fresh or frozen, for example, of the family of the Rosaceae, such as roses, and the family of the Rutaceae, such as *Citrus aurantium* (sour orange flower). One can also mention the use of flowers of other families, such as the flowers of the family of the Oleaceae such as *Jasminum officinalis* (jasmine) or the flowers of the family of the Asteraceae such as *Centaurea cyanus* (cornflower).

The seeds can also be used as starting plant material for obtaining an aqueous extract enriched with low molecular weight RNA. Any seed can be used, whole or in the form of a powder, germinated or ungerminated. For information and in a non-limiting manner, these seeds can originate from plants of the family of the Chenopodiaceae, such as *Quinoa chenopodium*, the family of the legumes or Fabaceae, such as *Lens esculenta* (lentil), or belonging to the family of the Poaceae, such as *Oryza sativa* (rice). They can also come from plants of the family of the Cucurbitaceae, such as *Cucurbita pepo* (squash), or of the Lamiaceae. Also usable for the invention are the small seeds or pips of the family of the Rutaceae or Rosaceae or any other species which produce fruits containing pips or stones.

The underground parts of a plant, such as the roots or the rhizomes, the bulbs can also be considered as starting plant material for obtaining an aqueous extract enriched with low molecular weight RNA. These underground parts can be in whole form, in the form of a powder, fresh, dried or frozen. For information and in a non-limiting manner, the roots or bulbs or rhizomes originate from the family of the Liliaceae, such as *Lilium candidum* or *Lilium tigrinum*, but for the invention one can also consider using any plant species from the family of the Iridaceae, the Amaryllidaceae, the Alliaceae.

It is also possible to consider as starting plant material for obtaining an aqueous extract enriched with low molecular weight RNA any type of leaf in whole form, in the form of a powder, fresh or frozen; one can mention the plants of the family of the Araliaceae or Dioscoreaceae or any other type of plant family which possesses a developed leaf system.

The plants used in the examples are preferably selected from the family of the Poaceae (formerly graminaceae), Fabaceae commonly referred to as legumes, Malvaceae, Bombacaceae, Cucurbitaceae, Chenopodiaceae or pseudo-cereal family, Rosaceae, Rutaceae, Liliaceae, Passifloraceae.

As non-limiting illustrative example, the plant material is selected from the species *Hibiscus esculentus* (okra), *Adansonia digitata* (baobab), *Chenopodium quinoa* (quinoa), *Lens esculenta* (lentil), *Oryza sativa* (rice), *Cucurbita pepo* (squash), *Rosa centifolia* (rose), *Citrus aurantium* (bitter orange tree), *Lilium candidum* (lily), *Lilium tigrinum* (tiger lily), *Passiflora alata* (winged-stem passion flower).

In a first step a) of the method according to the invention, the plant material is put in contact with water, preferably in a plant material/water ratio from 4 to 20% by weight/weight, more preferably in a ratio from 5 to 15%, for example, in a ratio of 5, 10 or 15% by weight/weight.

The water used is a distilled water, a demineralized water or else a water which is rich in mineral salts and/or rare-earth elements, preferably a distilled water.

Preferably, the plant material is crushed before it is put in contact with water in step a). Crushing is a mechanical action which allows a better extraction. Mechanical crushing, followed by alkaline lysis in the presence of EDTA, promotes the complete destructuring of the cell membrane and in particular of the nuclear membrane.

Then, in step b), tetrasodium EDTA is added to the mixture obtained in a). The pH in this step is alkaline and must be adjusted, if necessary, to a value between 10.5 and 11 by the addition of sodium hydroxide (NaOH). In step b), it is essential to maintain the alkaline pH between 10.5 and 11. Indeed, this pH level, associated with the action of the EDTA, causes the destructuring of the cell membrane, including the nuclear membrane, lysis of the cells, and denaturing of the DNA (the 2 strands of the double helix are separated). The pH check in step b) shows that the pH remains alkaline and stabilizes between 9 and 11.

The concentration of tetrasodium EDTA is preferably between 2 and 15 mM, and more preferably 10 mM.

This concentration is selected in order to optimize the yield of extraction of the low molecular weight RNA in the final extract. The tetrasodium EDTA will weaken and destructure the pecto-cellulose membranes of the plant cells by sequestering by complex formation of the divalent ions such as the calcium ions which form ionic bridges between the pectin molecules surrounding the cellulose microfibrils. The consequence of this is to promote the release of the cell content during the extraction. The step of treatment with EDTA is essential for enriching the extract with low molecular weight RNA.

The step of treatment with EDTA lasts preferably at least 1 h, at a temperature between 20 and 80° C. During this step, the mixture obtained in a) is advantageously stirred.

Then, in step c), the pH of the mixture obtained in b) is adjusted to a value between 6 and 8.

For example, the pH is adjusted by adding a hydrochloric acid (HCl) solution or any acid capable of regulating the pH which is compatible with a cosmetic use, such as citric acid or lactic acid.

This step of acidification causes the abrupt renaturation of the DNA (renewed pairing of the strands of the duplex). However, the renewed pairing of the very long chromosomal DNA does not occur completely, resulting in the formation of insoluble entanglements. In contrast, the much shorter small RNA remains in solution. The DNA and the small RNA are thus separated into two separate phases, a solid phase containing chromosomal DNA among other components and a liquid phase containing the small RNA among other components.

In a step d), the mixture obtained in c) is purified in such a manner as to eliminate the plant material and to recover an aqueous raw extract. Any method known to the person skilled in the art can be used. Preferably, the mixture obtained in c) is centrifuged at low speed, for example, for at least 10 min at 4000 g, in such a manner that the residual plant material settles in the pellet and an aqueous raw extract is recovered in the supernatant.

Advantageously, diatomaceous earth or silica at a concentration of 10 to 20 g/kg is added to the mixture before step d) so as to obtain a very compact pellet during the centrifugation, which makes it possible to obtain a supernatant which is free of undesirable solid matter.

In a step e), the pH is checked and readjusted to a value between 6 and 8. Preferably, the pH is readjusted to a value between 6 and 6.5, even more preferably to 6.5. The pH is readjusted by the addition of a solution of hydrochloric acid (HCl) or of sodium hydroxide (NaOH).

In fact, a pH below 6 can result in the precipitation of the nucleic acids in general, and thus the precipitation of low molecular weight RNA having a maximum length of 150 nucleotides. The pH adjustment step in step e) of the method according to the invention is a step which is indispensable for the optimal extraction of the low molecular weight RNA.

Advantageously, the readjustment of the pH of step e) is preceded by at least one filtration of the aqueous raw extract obtained in d). Preferably, successive filtrations will be carried out by lowering the filtration cutoff of 20 to 50 μm to 0.1 to 0.3 μm.

According to an advantageous embodiment, the method according to the invention comprises an additional hydrolysis step carried out before step c) either directly on the mixture obtained in b), or on the supernatant after centrifugation of the mixture obtained in b), and elimination of the plant material, by the action of at least one enzyme selected from a carbohydrase, a cellulase and/or a protease, preferably a protease, for at least 1 h, at a temperature between 45 and 65° C., and at a pH adjusted as a function of the enzyme(s) used, generally between 6 and 8.5.

When an additional hydrolysis step is carried out, the pH is then readjusted, if necessary, to between 6 and 8 and preferably between 6 and 6.5 in order to preserve the low molecular weight RNA extracted during the preceding steps and to prevent it from precipitating due to an excessively acidic pH.

In this advantageous embodiment, the method obligatorily comprises moreover a step of deactivation of the enzyme at a temperature between 65 and 80° C. for at least 1 h, this deactivation step being carried out directly after the hydrolysis step or between 2 of the successive filtration steps in e).

The second subject matter of the invention is an aqueous extract of plant material enriched with small RNA having a maximum length of 150 nucleotides of the invention which can be obtained by the method described above.

In a particular embodiment, the aqueous extract enriched with small RNA having a maximum length of 150 nucleotides of the invention is obtained by the method described above.

This extract contains no DNA (deoxyribonucleic acid).

Such an aqueous extract enriched with small RNA having a maximum length of 150 nucleotides comprises, before dilution, by weight relative to the total weight of the extract, 5 to 60 g/kg of dry extract, and 10 to 1000 mg/kg of small RNA having a maximum length of 150 nucleotides. The extract that can be obtained by the method according to the invention comprises moreover 0.5 to 30 g/kg of protein fragments and 0.5 to 50 g/kg of sugars. Such an extract can comprise moreover 0.01 to g/kg of amino acids and 0.01 to 4 g/kg of phenolic compounds.

The extract so obtained is considered to be concentrated. It can then be diluted in a physiologically acceptable solvent for a cosmetic use, in such a manner that the concentration of the extract is then adjusted to a particular dry extract weight of interest.

As illustrative and non-limiting examples of physiologically acceptable solvents, one can mention water, glycerol, ethanol, propanediol as well as its natural version called Zemea® originating from corn, butylene glycol, dipropylene glycol, the ethoxylated or propoxylated diglycols, cyclic polyols or any mixture of these solvents.

Preferably, the extract which can be obtained by the method according to the invention is diluted in a solvent such as 30% glycerol and water, and comprises, by weight relative to the total weight of the extract, 5 to 35 g/kg of dry extract, and 10 to 500 mg/kg of small RNA having a maximum length of 150 nucleotides. This diluted extract comprises moreover 0.5 to 20 g/kg of protein fragments and 0.5 to 30 g/kg of sugars. Such a diluted extract can comprise moreover 0.01 to 3 g/kg of amino acids, 0.01 to 2 g/kg of phenolic compounds.

For illustration, preferred embodiment examples of the method according to the invention are described below.

Example 1: Preparation of an Extract of Rice Germ (*Oryza sativa*) of the Family of the Poaceae, Enriched with Small RNA An aqueous extract enriched with low molecular weight RNA (having a maximum length of 150 nucleotides) is obtained from rice (*Oryza sativa*) from the family of the Poaceae (formerly graminaceae).

In a first step, 5% of rice germ in powder form are placed in distilled water, and 10 mM of tetrasodium EDTA are added, or 50 g of rice germ powder in 1 kg of distilled water and 3.8 g of tetrasodium EDTA. The pH in this step must be alkaline and between 10.5 and 11 for optimal enrichment of the extract with low molecular weight RNA.

The mixture is stirred for 2 h at ambient temperature.

An enzymatic hydrolysis is then carried out with proteases (consisting of Alcalase®, which is a serine endopeptidase, and bromelain) added at 2% each with respect to the plant material used, or 1 g of each enzyme is added to the mixture. The pH is adjusted to between 7.5 and 8.

The mixture is then heated for 2 h at 55° C., and then for 2 h at 80° C. to deactivate these same enzymes.

The mixture is then centrifuged with diatomaceous earth (10 g per 1 kg of mixture), for 10 min at 4000 g, to remove the solid matter.

After this step, the pH is checked, before optional dilution, in order to bring it to between 6 and 6.5, if necessary, and to preserve the small RNA of the extract.

Sequential filtrations through filters of decreasing porosity are then carried out so as to clarify the plant extract up to a sterilizing filtration at 0.2 μm.

In general, an aqueous extract of rice germ having a light yellow color and titrating at 20 to 50 g/kg of dry weight extract, 3 to 15 g/kg of protein fragments, 5 to 30 g/kg of sugars, 1.5 to 3 g/kg of amino acids, 300 to 750 mg/kg of phenolic compounds, and 50 to 400 mg/kg of low molecular weight RNA having a maximum length of 150 nucleotides.

Nevertheless, for rice germ from the species *Oryza sativa*, the extracts obtained can exhibit considerable variability depending on factors such as site of harvest, year of harvest, season, climatic conditions, etc.

More particularly, in this example, one obtains an aqueous extract titrating at 23 g/kg of dry weight extract. The physico-chemical analysis shows that this extract has a concentration of 4.8 g/kg of protein fragments, 8.2 g/kg of sugars, 2.3 g/kg of amino acids, 328 mg/kg of phenolic compounds, and 132 mg/kg of low molecular weight RNA having a maximum length of 150 nucleotides. This extract can subsequently be diluted in water and preserved by addition of a cosmetic solvent such as glycerol and of a preservative such as 1.5% phenoxyethanol.

Example 2: Study of the Influence of the pH and of the Enzymatic Hydrolysis in the Implementation of the Method In order to study the influence of the pH in the implementation of the method according to the invention, extraction tests were carried out at different pH values and for different types of plants.

These extractions were carried out in particular on rice germ (as described in example 1). Comparable results can be obtained in general for all types of plants considered and more particularly described according to the invention.

5% of rice germ powder are placed in water, or 50 g of rice germ powder in 1 kg of distilled water, and 10 mM of tetrasodium EDTA are added (or 3.8 g). The pH was adjusted to 7 or to 11 by adding between 1 and 3 mL of concentrated sodium hydroxide; then the mixture is stirred for 2 h at ambient temperature.

Sample collections are then carried out during the extraction method in order to observe the enrichment with low molecular weight RNA for each extract after this key step.

An electrophoresis on agarose gel at 2% is thus carried out in order to visualize the presence of the low molecular weight RNA (FIG. 1A).

As illustrated in FIG. 1A, it can be observed that the optimal pH for enriching the extract with low molecular weight RNA is an alkaline pH of 11; in fact, at pH 7, the extract contains no low molecular weight RNA (absence of characteristic band).

The use of an alkaline pH during the step of treatment with EDTA is thus an essential condition for the implementation of the method according to the invention.

In a second step, an enzymatic hydrolysis is carried out with proteases (consisting of Alcalase® and bromelain) at 2% each with respect to the plant material used, or 1 g of each enzyme, in the mixture. The pH is adjusted to between 7.5 and 8, optimal pH for activity of the enzymes and optimal for keeping the low molecular weight RNA soluble in the mixture, since a pH of less than 6 causes it to precipitate.

The mixture is then heated for 2 h at 55° C., the optimal temperature for activity of the enzymes, and then for 2 h at 80° C. to deactivate these same enzymes.

The mixture is then centrifuged with diatomaceous earth (10 g per 1 kg of mixture), for 10 min at 4000 g, in order to remove the solid matter.

After this step, the pH is checked, before optional dilution, in order to bring it to between 6 and 6.5 and to preserve the small RNA of the extract.

Sequential filtrations through filters of decreasing porosity are then carried out in order to clarify the plant extract up to a sterilizing filtration of porosity 0.2 μm.

The final extract is visualized by electrophoresis on agarose gel at 2% (FIG. 1B).

As illustrated in FIG. 1B, one notes that the use of enzyme(s) advantageously improves the yield of extraction of the low molecular weight RNA in the final extract.

This result was observed on different types of plant extracts. The fact that the enzymes potentiate the extraction of low molecular weight RNA could be due to the fact that proteins are often bound to the nucleic acids; the degradation of the proteins by enzymes which break the peptide bonds of the proteins, thus creating protein fragments having small sizes (less than 10 kDa), would make it possible to dissociate the RNA bound to the proteins and release it, thus increasing its final yield in the extract.

Example 3: Preparation of an Extract of Lentils (*Lens Esculenta*) from the Family of the Fabaceae, Enriched with Small RNA An aqueous extract enriched with low molecular weight RNA (having a maximum length of 150 nucleotides) is obtained from lentils (*Lens esculenta*).

In a first step, the lentils are allowed to germinate the day before the extraction method, namely 40 g of lentils covered with distilled water.

The next day, distilled water is added in order to obtain the equivalent of 4% of lentils used in the extraction method.

The lentils (40 g in sufficient quantity for 1 kg of distilled water) are then crushed, and 10 mM of tetrasodium EDTA (or 3.8 g) is added. The pH is adjusted to 11 by addition of a solution of NaOH, and the mixture is stirred for 2 h at ambient temperature.

A filtration with large porosity is advantageously carried out to remove the solid debris.

Proteases (2% of bromelain and 2% of Alcalase® with respect to the plant material used) are then added to the filtrate in order to carry out an enzymatic hydrolysis, taking care to allow the enzymes to solubilize before adjusting the pH to between 7.5 and 8 by addition of a solution of HCl.

The filtrate is maintained under stirring for 2 h at 55° C., the time during which the hydrolysis takes place.

Sequential filtrations are then carried out through filters of decreasing porosity having sizes between 20 and 50 µm, then between 7 and 20 µm in order to clarify the aqueous raw plant extract.

The extract is then heated for 1 h at 80° C. in order to deactivate the enzymes.

The filtrations are continued up to a porosity of 0.3 to 0.4 µm.

In this step of the extraction method, it is important to properly check the pH, before optional dilution, in order to bring it advantageously to between 6 and 6.5 and to preserve the small RNA of the extract.

In general, one obtains an aqueous extract of lentils having an amber-red color, titrating at 15 to 25 g/kg of dry weight extract, 3 to 8 g/kg of protein fragments, 2 to 8 g/kg of sugars, 1 to 3 g/kg of amino acids, 300 to 750 mg/kg of phenolic compounds, and 50 to 150 mg/kg of low molecular weight RNA having a maximum length of 150 nucleotides.

However, for lentils of the same species (*Lens esculenta*), the extracts obtained can exhibit considerable variability depending on factors such as site of harvest, year of harvest, season, climatic conditions, etc.

More particularly, in this example, one obtains an aqueous extract titrating at 15.4 g/kg: of dry weight extract, 6.9 g/kg of protein fragments, 2.1 g/kg of sugars, 1.4 g/kg of amino acids, 400 mg/kg of phenolic compounds, and 96 mg/kg of low molecular weight RNA having a maximum length of 150 nucleotides.

The extract is then diluted in water or in a physiologically acceptable solvent comprising, for example, water and 30% glycerol, in such a manner that the final extract is adjusted to 10 g/kg of dry weight extract.

The physico-chemical analysis shows that, after dilution, this extract has a concentration of protein fragments of 5.1 g/kg, of sugars of 1.5 g/kg, of amino acids of 0.8 g/kg, of phenolic compounds of 280 mg/kg, and of low molecular weight RNA (having a maximum length of 150 nucleotides) of 70 mg/kg as illustrated more particularly in FIG. 2 by the quantification of the low molecular weight RNA with the Bioanalyseur® (Agilent).

The Bioanalyseur® is an apparatus which makes it possible to run miniaturized electrophoreses thanks to electronic chips specific for the analysis of nucleic acids such as the analysis of low molecular weight RNA. It makes it possible to determine the size and the concentration contained in an extract using a few microliters. The result is in the form of a graph with an arbitrary fluorescence unit on the ordinate (FU) and the number of nucleotides (nt) on the abscissa. An internal marker is added to each analysis (peak at 4 nt in FIG. 2) and serves as internal control for validating the proper running of the analysis.

Example 4: Test Pertaining to the Absence of DNA in the Extract According to Example 3 (Lentils)

In order to verify that the nucleic acid obtained in the extracts according to the invention is in fact RNA and more particularly low molecular weight RNA (having a maximum length of 150 nucleotides) and not DNA, a test using a DNase (OPTIZYME™ Fisher Bioreagent) which specifically degrades the DNA was carried out following the protocol recommended by the supplier.

A control solution containing 500 µg/mL of salmon DNA (Sigma, 31149-10g-F) and another control solution containing 500 µg/mL of low molecular weight RNA originating from the Torula yeast (Sigma R6625-25G) were prepared. The reaction volume contains per 1 µg of DNA or RNA, 1 µL of RNase, 1 µL of buffer 10× and completed to 10 µL with DEPC (diethyl pyrocarbonate) water 0.1% v/v. The reaction mixture is then incubated for 30 min at 37° C., optimal condition for reaction of the DNase. The enzyme is then deactivated by adding 50 mM of tetrasodium EDTA and by heating for 10 min at 65° C.

To visualize the profile of the control solutions and of the extract according to example 3 after action of the DNase, the small RNA is quantified with the Bioanalyseur®, before and after treatment with the DNase. The profiles obtained with or without treatment of the plant extract with the DNase are identical, the quantity remaining the same or approximately 30 mg/kg, as illustrated in FIG. 3. An internal marker is added to each analysis (peak at 4 nt in FIG. 3) and serves as internal control for validating the proper running of the analysis.

The test with the DNase, an enzyme which specifically degrades DNA and not RNA, demonstrates that the nucleic acid of the extract according to example 3 is still present after the treatment with the DNase. It is thus in fact RNA, in particular low molecular weight RNA having a maximum length of 150 nucleotides, and not DNA.

Example 5: Preparation of an Extract of Okra (*Hibiscus Esculentus*) from the Family of the Malvaceae, Enriched with Small RNA An aqueous extract enriched with low molecular weight RNA (having a maximum length of 150 nucleotides) is obtained from okra fruits of the species *Hibiscus esculentus*.

In a first step, after thawing, 10% of *Hibiscus esculentus* fruits are mixed in distilled water, or, for example, 100 g of fruits in 1 kg of distilled water, and are then crushed for 10 minutes with addition of tetrasodium EDTA at a final concentration of 10 mM or 3.8 g per 1 kg. The pH in this step is between 10.5 and 11, optimal pH for enriching the extract with small RNA.

This mixture is then stirred for 2 h at 45°. Even if the temperature at this stage can vary from 20° C. to 80° C., for this species, a temperature of 45° C. turns out to be the temperature which makes it possible to obtain the best results in terms of enrichment of the final aqueous extract with low molecular weight RNA.

After the 2 h, diatomaceous earth (or silica) is added at a concentration of 10 g/kg, and the mixture is stirred for another 10 min, followed by a centrifugation at 4000 g for 10 min.

The supernatant is then harvested. This raw extract contains in particular protein fragments, sugars, and low molecular weight RNA.

Proteases (2% of bromelain and 2% of Alcalase® with respect to the quantity of plant material used) are added in order to carry out an enzymatic hydrolysis, taking care to allow the enzymes to solubilize before adjusting the pH to between 7.5 and 8.

The raw solution is kept under stirring for 2 h at 55° C., the time during which the hydrolysis takes place. The enzymatic hydrolysis will make it possible to obtain low molecular weight protein fragments (less than 10 kDa, the high molecular weight proteins possibly being allergenic). Such protein fragments obtained in this manner can moreover have an interesting biological activity with regard to the skin.

To start the clarification of the raw extract, sequential filtrations are then carried out using filters of decreasing porosity having sizes between 20 and 50 μm, then 7 and 20 μm, followed by a step of heating of the extract at high temperature at 80° C. overnight. This step makes it possible to deactivate the proteases which, under the action of strong heat, undergo denaturation and then become inactive.

The filtrations are then continued up to a sterilizing filtration at 0.1 to 0.3 μm.

The plant extract then must have a final pH between 6 and in order to prevent the low molecular weight RNA from precipitating. In this step of the extraction method, the pH indeed must be verified, before optional dilution, in order to bring it even more preferably to between 6 and 6.5.

In general, one obtains an aqueous extract having a pale yellow color titrating at 10 to 20 g/kg of dry weight extract, 2 to 5 g/kg of protein fragments, 2.5 to 5 g/kg of sugars, 0.1 to 2 g/kg of amino acids, 0.2 to 3 g/kg of phenolic compounds, and 10 to 100 mg/kg of low molecular weight RNA having a maximum length of 150 nucleotides.

Nevertheless, for okra fruits from the same species (*Hibiscus esculentus*), the extracts obtained can exhibit considerable variability depending on factors such as site of harvest, year of harvest, season, climatic conditions, etc.

In this example, one obtains more particularly an aqueous extract which titrates at 13.3 g/kg of dry weight extract, 3.2 g/kg of protein fragments, 3.9 g/kg of sugars, 790 mg/kg of amino acids, 490 mg/kg of phenolic compounds, and 60 mg/kg of low molecular weight RNA having a maximum length of 150 nucleotides.

The extract is then diluted in a physiologically acceptable solvent comprising, for example, water and 30% of glycerol, in such a manner that the final extract is adjusted to 10 g/kg of dry weight extract.

The physico-chemical analysis shows that, after dilution, the extract has a concentration of protein fragments of 2.5 g/kg, of sugars of 2.7 g/kg, of amino acids of 520 mg/kg, of phenolic compounds of 320 mg/kg and of 35 mg/kg of low molecular weight RNA having a maximum length of 150 nucleotides.

Example 6: Demonstration of the Role of a Step of Treatment with EDTA in the Implementation of the Method of Extraction of Small RNA from Okra (*Hibiscus Esculentus*)

For the purpose of demonstrating the role of a step of treatment with EDTA in the extraction of low molecular weight RNA, an extract of *Hibiscus esculentus* fruits was obtained by modifying certain essential steps of the method according to the invention, making it impossible to enrich the extract with low molecular weight RNA.

15% of thawed *Hibiscus esculentus* fruits are mixed with distilled water, and are then crushed, or 150 g of fruits in 1 kg of distilled water.

Proteases are then added sequentially: 2% of Alcalase® with respect to the plant material used (or 3 g) at pH 8 for 2 h at 55° C. (optimal condition for this enzyme), then 2% of bromelain (or 3 g) at a pH adjusted to a value between 4 and 4.5 for 2 h at 55° C.

This mixture is then centrifuged to remove the solid debris.

In order to start the clarification of the raw extract, sequential filtrations are then carried out through filters of decreasing porosity having sizes between 20 and 50 μm, then 7 and 20 μm, followed by a step of heating of the extract at high temperature at 80° C. overnight.

The filtrations are continued up to a sterilizing filtration at 0.1 to 0.3 μm.

The aqueous extract obtained is then diluted in a physiologically acceptable solvent comprising, for example, water and 30% glycerol, to reach 9.6 g/kg of dry weight extract. The pH of the final extract is between 4 and 4.5.

The physico-chemical analysis shows that the final plant extract, after dilution, has a concentration of protein fragments of 2.2 g/kg, of sugars of 3.8 g/kg, 550 mg/kg of amino acids, and 243 mg/kg of phenolic compounds.

The analysis with the Bioanalyseur® indicates that the concentration of low molecular weight RNA is zero for this extract. This result demonstrates that an extract obtained based on an extraction method which has no step of treatment with EDTA contains no low molecular weight RNA. The step of treatment with EDTA is consequently essential for obtaining an extract rich in low molecular weight RNA according to the invention.

Example 7: Preparation of an Extract of Baobab (*Adansonia Digitata*) from the Family of the Bombacaceae, Enriched with Small RNA An aqueous extract enriched with low molecular weight RNA (having a maximum length of 150 nucleotides) is obtained from baobab of the species *Adansonia digitata*.

In a first step, 5% of baobab seed oilcake (*Adansonia digitata*) are crushed dry or directly in water containing tetrasodium EDTA at a final concentration of 10 mM, or 50 g of baobab oilcake in 1 kg of distilled water, to which 3.8 g of tetrasodium EDTA are added. The pH in this step is alkaline and more particularly between 10.5 and 11, optimal pH for enriching the extract with low molecular weight RNA.

The mixture is stirred for 2 h at 58° C.

For this species, advantageously, a hydrolysis step with a proteolytic enzyme is carried out: 2% of papain are added with respect to the quantity of plant material used (or 1 g). If necessary, the pH of the mixture is adjusted to between 7 and and the mixture is stirred for 2 h at 58° C., optimal conditions for this enzyme.

Then, the pH is adjusted to 8, and then the extract is centrifuged for 10 min at 4000 g in order to remove the solid matter.

Sequential filtrations are then carried out through filters of decreasing porosity having sizes between 20 and 50 μm, then 7 and 20 μm in order to clarify the plant extract.

The extract is then heated at 80° C. for between 8 and 12 hours in order to thermally deactivate the enzyme.

The filtrations are continued up to a porosity of 0.3 to 0.4 μm. In this step of the extraction method, the pH must be verified properly, before optional dilution, in order to bring it to between 6 and 6.5 and to preserve the small RNA of the extract. In general, an acidic pH can result in the precipitation of the nucleic acids and thus also in the precipitation of the low molecular weight RNA.

In general, an aqueous extract of baobab having an amber-red color is obtained, which titrates at 15 to 25 g/kg of dry weight extract, 3 to 8 g/kg of protein fragments, 2 to 8 g/kg of sugars, 0.05 to 1 g/kg of amino acids, 0.05 to 1 g/kg of phenolic compounds, and 10 to 80 mg/kg of low molecular weight RNA having a maximum length of 150 nucleotides.

However, extracts obtained from the species *Adansonia digitata* can exhibit considerable variability depending on factors such as site of harvest, year of harvest, season, climatic conditions, etc.

In this example, more particularly, an aqueous extract is obtained, which titrates at 17 g/kg of dry weight extract, 5.3 g/kg of protein fragments, 5.4 g/kg of sugars, 650 mg/kg of amino acids, 441 mg/kg of phenolic compounds, and 57 mg/kg of low molecular weight RNA having a maximum length of 150 nucleotides.

The extract is then diluted in a mixture of water and 30% of glycerol, and 1.5% of phenoxyethanol are added, which makes it possible to obtain a final extract at 12 g/kg of dry weight extract.

The physico-chemical analysis shows that, after dilution, this extract has a concentration of protein fragments of 2.9 g/kg, of sugars of 4 g/kg, of amino acids of 400 mg/kg, of phenolic compounds of 310 mg/kg, and of 41 mg/kg of low molecular weight RNA having a maximum length of 150 nucleotides.

Example 8: Demonstration of the Role of a Step of Treatment with EDTA for the Implementation of a Method of Extraction of Small RNA from Baobab (*Adansonia digitata*)

For the purpose of demonstrating the role of a step of treatment with EDTA in the extraction of the low molecular weight RNA, an extract of baobab (*Adansonia digitata*) was also obtained by modifying certain essential steps of the method according to the invention, making it impossible to enrich the extract with low molecular weight RNA.

In a first step, 10% of baobab seed oilcake (*Adansonia digitata*) are crushed, then water is added, or 100 g of baobab cake in 1 kg of distilled water.

For this species, a hydrolysis with a proteolytic enzyme is carried out: 2% of papain are added with respect to the quantity of plant material used, or 2 g. The pH is adjusted to between 7 and 8, and the mixture is stirred for 2 h at 58° C., optimal conditions for the activity of the enzyme. After this period, the pH is lowered to 4.5, a pH routinely used for cosmetic ingredients.

Subsequently, the extract is centrifuged for 10 min at 4000 g to remove the solid matter. The extract is then heated at 80° C. for between 8 and 12 h in order to deactivate the enzyme by high temperature.

Sequential filtrations are then carried out through filters of decreasing porosity having sizes between 20 and 50 μm, then up to a porosity of 0.3 to 0.4 μm.

An extract having a clear yellow color is then obtained, which titrates at 12.5 g/kg of dry weight extract, 5.8 g/kg of protein fragments, 7.6 g/kg of sugars, 540 mg/kg of amino acids, and 440 mg/kg of phenolic compounds.

The extract is then diluted in water and glycerol in such a manner as to obtain a final extract containing 30% of glycerol, and is adjusted to 10 g/kg of dry weight extract.

The physico-chemical analysis shows that, after dilution, the plant extract has a concentration of protein fragments of 3.25 g/kg, of sugars of 5.1 g/kg, of amino acids of 310 mg/kg, and of phenolic compounds of 250 mg/kg. Under these extraction conditions (absence of treatment with EDTA), the analysis with the Bioanalyseur® indicates that the concentration of low molecular weight RNA is zero for this extract. This result confirms that an extract obtained using an extraction method without treatment with EDTA (at alkaline pH) contains no low molecular weight RNA. The step of treatment with EDTA is essential for obtaining an extract which is rich in low molecular weight RNA according to the invention.

Example 9: Study of the Influence of the Final pH in the Preparation of Extracts of Okra (*Hibiscus esculentus*) and of Baobab (*Adansonia digitata*)

The extraction method is carried out under the same operating conditions as in examples 5 and 7, in order to enrich an extract with low molecular weight RNA, except for the final pH adjustment step.

This extraction method is carried out with tetrasodium EDTA treatment step, followed by the enzymatic hydrolysis step, but with a final adjustment of the extract to an acidic pH between 4 and 4.5 instead of a pH between 6 and 8.

This results in the precipitation of the low molecular weight RNA, results which are confirmed by the analysis with the Bioanalyseur®, which gives a concentration of zero low molecular weight RNA for each one of the extracts of okra (*Hibiscus esculentus*) and of baobab (*Adansonia digitata*) thus obtained.

Example 10: Preparation of an Extract of Squash (*Cucurbita Pepo*) from the Family of the Cucurbitaceae, Enriched with Small RNA An aqueous extract enriched with low molecular weight RNA (having a maximum length of 150 nucleotides) is obtained from squash (*Cucurbita pepo*) from the family of the Cucurbitaceae.

In a first step, 10% of squash seed oilcake are mixed with water, and tetrasodium EDTA is added to obtain a final concentration of 10 mM, or 100 g squash oilcake in 1 kg of distilled water and 3.8 g of tetrasodium EDTA.

The pH in this step must be alkaline and more particularly between 10.5 and 11 for an optimal enrichment of the extract with low molecular weight RNA.

The mixture is stirred for 2 h at 45° C.

An enzymatic hydrolysis is then carried out with proteases: 2% of Alcalase® and 4% of papain with respect to the quantity of plant material used, or 2 g of Alcalase® and 4 g of papain are thus added to the mixture. The pH is adjusted to between 7.5 and 8, optimal pH of activity for these two enzymes, this pH also being optimal for keeping the low molecular weight RNA soluble in the mixture, since a pH of less than 6 can cause them to precipitate.

The mixture is then heated for 2 h at 50° C., optimal temperature for activity of the enzymes, then for 2 h at 80° C. to deactivate these same enzymes.

The mixture is then centrifuged with diatomaceous earth (10 g per 1 kg of mixture), for 10 min at 4000 g, in order to remove the solid matter.

After this step, the pH is checked, before optional dilution, in order to bring it, if necessary, to between 6 and 6.5 and to preserve the small RNA of the extract.

Sequential filtrations are then carried out through filters of decreasing porosity having sizes between 20 and 50 µm, then 7 and 20 µm in order to clarify the plant extract. Then, the filtrations are continued up to the sterilizing filtration at 0.2 µm.

In general, an aqueous extract having a light yellow color is obtained, which titrates at 20 to 50 g/kg of dry weight extract, 3 to 25 g/kg of protein fragments, 1 to 10 g/kg of sugars, and 50 to 250 mg/kg of low molecular weight RNA having a maximum length of 150 nucleotides.

However, for squash of the same species (*Cucurbita pepo*), the extracts obtained can exhibit considerable variability depending on factors such as site of harvest, year of harvest, season, climatic conditions, etc.

In this example, more particularly, an aqueous extract is obtained, which titrates at 37.3 g/kg of dry weight extract, 18.4 g/kg of protein fragments, 3.8 g/kg of sugars, and 168 mg/kg of low molecular weight RNA having a maximum length of 150 nucleotides.

The extract can then be diluted in a physiologically acceptable solvent comprising, for example, water and 30% of glycerol.

Example 11: Preparation of an Extract of *Quinoa* (*Chenopodium Quinoa*) from the Family of the Chenopodiaceae or Pseudocereal Family, Enriched with Small RNA An aqueous extract enriched with low molecular weight RNA (having a maximum length of 150 nucleotides) is obtained from *quinoa Chenopodium quinoa* from the family of the Chenopodiaceae or pseudocereal family.

In a first step, the germinated *quinoa* seeds (10% of final weight, or 100 g) are used in the extraction process and are mixed in 1 kg of distilled water, and are then crushed, and tetrasodium EDTA is added in order to obtain a final concentration of 10 mM or 3.8 g. The pH in this step has to be alkaline and between 10.5 and 11, the pH being thus adjusted with NaOH, for optimal enrichment of the extract according to the invention with low molecular RNA having a maximum length of 150 nucleotides. The mixture is stirred for 2 h at 55° C.

An enzymatic hydrolysis is then carried out with proteases: 2% of Alcalase® and 2% of bromelain are added to the mixture (with respect to the material used). The pH is adjusted to between 7.5 and 8, optimal pH of activity for these two enzymes, this pH also being optimal for keeping the low molecular weight RNA soluble in the mixture, a pH of less than 6 causing it to precipitate.

The mixture is heated for 2 h at 45° C., optimal temperature for activity of the enzymes.

The mixture is then centrifuged with diatomaceous earth (10 g per 1 kg of mixture), for 10 min at 4000 g, to remove the solid matter.

Then, the filtrate is heated for 2 h at 80° C. in order to deactivate these enzymes.

Sequential filtrations are then carried out through filters of decreasing porosity having sizes between 20 and 50 µm, then 7 and 20 µm in order to clarify the plant extract.

After this filtration step, a dilution of the extract can be carried out preferably in water and glycerol in such a manner as to obtain a final extract containing 30% of glycerol.

Then, the filtrations are continued up to the sterilizing filtration at 0.2 µm.

In general, an extract having a light yellow color is obtained, which titrates at 20 to 50 g/kg of dry weight extract, 3 to 15 g/kg of protein fragments, 10 to 30 g/kg of sugars, 0.5 to 5 g/kg of amino acids, 100 to 700 mg/kg of phenolic compounds, and 50 to 250 mg/kg of low molecular weight RNA having a maximum length of 150 nucleotides.

Similar results can be obtained from ungerminated *quinoa* seeds or from *quinoa* flour.

Nevertheless, for *quinoa* of the same species (*Chenopodium quinoa*), the extracts obtained can exhibit considerable variability depending on factors such as site of harvest, year of harvest, season, climatic conditions, etc.

More particularly, in this example, an aqueous extract is obtained, which titrates at 33 g/kg of dry weight extract, 9.5 g/kg of protein fragments, 21.6 g/kg of sugars, 1.8 g/kg of amino acids, 364 mg/kg of phenolic compounds, and 173 mg/kg of low molecular weight RNA having a maximum length of 150 nucleotides.

The extract can then be diluted in a physiologically acceptable solvent comprising, for example, water and 30% of glycerol.

Example 12. Preparation of an Extract of Rose (*Rosa Centifolia*) from the Family of the Rosaceae, Enriched with Small RNA An aqueous extract enriched with low molecular weight RNA (having a maximum length of 150 nucleotides) is obtained from rose (*Rosa centifolia*) of the family of the Rosaceae. In this example, the whole fresh flower is used.

In a first step, 10% of roses are mixed in distilled water, or, for example, 100 g of flowers completed to 1 kg with distilled water, and are then crushed for 10 minutes with addition of tetrasodium EDTA at a final concentration of 10 mM, or 3.8 g per 1 kg. The pH in this step is between 10.5 and 11, optimal pH for enriching the extract with small RNA.

This mixture is then stirred for 1 h at 80° C. Even if the temperature at this stage can vary from 50° C. to 80° C., for this species, a temperature of 80° C. is found to be the temperature which makes it possible to obtain the best results in terms of enrichment of the final aqueous extract with low molecular weight RNA.

After this step, sequential filtrations are then carried out through filters of decreasing porosity with sizes between 20 and 50 µm, then 7 and 20 µm, in order to remove the solid matter and then clarify the plant extract.

In this step, the pH is checked, in order to bring it, if necessary, to between 6 and 6.5 and to preserve the small RNA of the extract.

Then, the filtrations are continued up to the sterilizing filtration at 0.2 µm.

In general, an aqueous extract having an amber color is obtained, which titrates at 5 to 20 g/kg of dry weight extract, 1 to 10 g/kg of protein fragments, 1 to 10 g/kg of sugars, 0.5 to 2 g/kg of phenolic compounds, and 20 to 200 mg/kg of low molecular weight RNA having a maximum length of 150 nucleotides.

Nevertheless, for roses of the same species (*Rosa centifolia*), the extracts obtained can exhibit considerable variability depending on factors such as site of harvest, year of harvest, season, the climatic conditions, etc.

In this example, more particularly, an aqueous extract is obtained, which titrates at 11.3 g/kg of dry weight extract, 5.1 g/kg of protein fragments, 2.6 g/kg of sugars, 1 g/kg of phenolic compounds, and 96 mg/kg of low molecular weight RNA having a maximum length of 150 nucleotides.

The extract can then be diluted with, for example, 30% glycerol, which makes it possible to obtain a final extract at 8 g/kg of dry weight extract.

The physico-chemical analysis shows that, after dilution, this extract has a concentration of protein fragments of 4.6 g/kg, of sugars of 2 g/kg, of amino acids of 280 mg/kg, of phenolic compounds of 800 mg/kg, and of 83 mg/kg of low molecular weight RNA having a maximum length of 150 nucleotides.

Example 13: Preparation of an Extract of the Bitter Orange Flowers (*Citrus aurantium*) from the Family of the Rutaceae, Enriched with Small RNA An aqueous extract enriched with low molecular weight RNA (having a maximum length of 150 nucleotides) is obtained from bitter orange flowers (*Citrus aurantium*) from the family of the Rutaceae. In this example, the whole fresh flower is used.

In a first step, 5% of bitter orange flowers are mixed in the distilled water, or, for example, 50 g of flowers completed to 1 kg with distilled water, and then crushed for 5 minutes with addition of tetrasodium EDTA at a final concentration of 10 mM, or, 3.8 g per 1 kg. The pH in this step is between 10.5 and 11, optimal pH for enriching the extract with small RNA.

This mixture is then stirred for 1 h at 45° C. Even if the temperature at this stage can vary from 25° C. to 50° C., for this species, a temperature of 45° C. is found to be the temperature which makes it possible to obtain the best results in terms of enrichment of the final aqueous extract with low molecular weight RNA.

After this step, sequential filtrations are then carried out through filters of decreasing porosity having sizes between 20 and 50 µm, then 7 and 20 µm, in order to remove the solid matter and then to clarify the plant extract.

In this step, the pH is checked, in order to bring it, if necessary, to between 6 and 6.5 and to preserve the small RNA of the extract.

The filtrations are then continued up to a porosity at 0.3 to 0.5 µm.

In general, an aqueous extract having an amber color is obtained, which titrates at 5 to 20 g/kg of dry weight extract, 1 to 10 g/kg of protein fragments, 1 to 10 g/kg of sugars, 200 to 1000 mg/kg of phenolic compounds, and 10 to 100 mg/kg of low molecular weight RNA having a maximum length of 150 nucleotides.

Nevertheless, for flowers of the same species (*Citrus aurantium*), the extracts obtained can exhibit considerable variability depending on factors such as time of harvest, year of harvest, season, climatic conditions, etc.

In this example, more particularly, an aqueous extract is obtained, which titrates at 11.8 g/kg of dry weight extract, 4.5 g/kg of protein fragments, 3.8 g/kg of sugars, 560 mg/kg of phenolic compounds, and 20 mg/kg of low molecular weight RNA having a maximum length of 150 nucleotides.

The extract can then be diluted in a physiologically acceptable solvent such as water or glycerol.

Example 14: Preparation of an Extract of Lily (*Lilium candidum*), Enriched with Small RNA An aqueous extract enriched with low molecular weight RNA (having a maximum length of 150 nucleotides) is obtained from white lily bulb (*Lilium candidum*) of the family of the Liliaceae.

In a first step, 15% of lily bulbs are placed in distilled water, or, for example, 150 g of bulbs in 1 kg of distilled water containing tetrasodium EDTA at a final concentration of 10 mM, or, 3.8 g per 1 kg; then the crushing of the solution is carried out for 5 min. The pH in this step is between 10.5 and 11, optimal pH for enriching the extract with small RNA.

This mixture is then stirred for 30 minutes at 65° C. Even if the temperature at this stage can vary from 50° C. to 80° C. and the stirring time can vary from 30 minutes to 1 h, for this species, a temperature of 65° C. for 30 minutes is found to constitute the conditions which make it possible to obtain the best results in terms of enrichment of the final aqueous extract with low molecular weight RNA.

After this step, sequential filtrations are then carried out through filters of decreasing porosity having sizes between 20 and 50 µm, then 7 and 20 µm, in order to remove the solid matter and then clarify the plant extract.

In this step, the pH is checked, in order to bring it, if necessary, to between 6 and 6.5 and to preserve the small RNA of the extract.

The filtrations are continued up to a porosity of 2 to 4 µm. The extract can then be stored thanks to the addition of 30% of glycerol and 1.5% of phenoxyethanol. The filtrations are continued up to a porosity of 0.2 to 0.3 µm.

In general, an aqueous extract having a yellow color is obtained, which titrates at 10 to 25 g/kg of dry weight extract, 0.5 to 5 g/kg of protein fragments, 2 to 15 g/kg of sugars, 100 to 500 mg/kg of phenolic compounds, and 10 to 100 mg/kg of low molecular weight RNA having a maximum length of 150 nucleotides.

Nevertheless, for lilies of the same species (*Lilium candidum*), the extracts obtained can exhibit considerable variability depending on factors such as site of harvest, year of harvest, season, climatic conditions, etc.

More particularly, in this example, an aqueous extract is obtained, which titrates at 16.3 g/kg of dry weight extract, 1.5 g/kg of protein fragments, 5.3 g/kg of sugars, 200 mg/kg of phenolic compounds, and 20 mg/kg of low molecular weight RNA having a maximum length of 150 nucleotides.

The extract can then be diluted in a physiologically acceptable solvent such as water or glycerol.

Example 15: Preparation of an Extract of Lily (*Lilium Tigrinum*) from the Family of the Liliaceae, Enriched with Small RNA An aqueous extract enriched with low molecular weight RNA (having a maximum length of 150 nucleotides) is obtained from tiger lily bulb (*Lilium tigrinum*) of the family of the Liliaceae.

In a first step, after washing and thawing, 10% of lily bulbs are mixed in distilled water, or, for example, 100 g of bulbs in 1 kg of distilled water containing tetrasodium EDTA at a final concentration of 10 mM, or, 3.8 g per 1 kg, and then the mixture is crushed for 5 minutes. The pH in this step is between 10.5 and 11, optimal pH for enriching the extract with small RNA.

This mixture is then stirred for 1 hour at 80° C. Even if the temperature at this stage can vary from 50° C. to 80° C. and the stirring time from 30 minutes to 1 h, for this species, a temperature of 80° C. for 1 hour is found to constitute the conditions which make it possible to obtain the best results in terms of enrichment of the final aqueous extract with low molecular weight RNA.

After this step, sequential filtrations are then carried out through filters of decreasing porosity having sizes between 20 and 50 µm, then 7 and 20 µm, in order to remove the solid matter and then clarify the plant extract.

In this step, the pH is checked, in order to bring it, if necessary, to between 6 and 6.5 and to preserve the small RNA of the extract. The filtrations are continued up to a porosity of 0.2 to 0.3 µm.

In general, an aqueous extract having a yellow color is obtained, which titrates at 10 to 25 g/kg of dry weight extract, 0.5 to 5 g/kg of protein fragments, 5 to 20 g/kg of sugars, 100 to 500 mg/kg of phenolic compounds, and 10 to 100 mg/kg of low molecular weight RNA having a maximum length of 150 nucleotides.

Nevertheless, for lilies of the same species (*Lilium tigrinum*), the extracts obtained can exhibit considerable variability depending on factors such as site of harvest, year of harvest, season, climatic conditions, etc.

More particularly, in this example, an aqueous extract is obtained, which titrates at 17.9 g/kg of dry weight extract, 2.1 g/kg of protein fragments, 11.4 g/kg of sugars, 200 mg/kg of phenolic compounds, and 54 mg/kg of low molecular weight RNA having a maximum length of 150 nucleotides.

The extract is then diluted in a mixture of water, 30% glycerol and 1.5% phenoxyethanol, which makes it possible to obtain a final extract at 10 g/kg of dry matter.

The physico-chemical analysis shows that, after dilution, this extract has a concentration of protein fragments of 1.0 g/kg, of sugars of 5.8 g/kg, of phenolic compounds of 100 mg/kg, and of 30 mg/kg of low molecular weight RNA having a maximum length of 150 nucleotides.

Example 16: Preparation of an Extract of Passion Fruit (*Passiflora alata*) from the Family of the Passifloraceae, Enriched with Small RNA An aqueous extract enriched with low molecular weight RNA (having a maximum length of 150 nucleotides) is obtained from passion fruit (*Passiflora alata*) of the family of the Passifloraceae.

In a first step, 5% of fruit powder are mixed in distilled water, or, for example, 50 g of fruit powder completed to 1 kg with distilled water; then the solution is stirred for 5 minutes, then tetrasodium EDTA is added at a final concentration of 10 mM, or 3.8 g per 1 kg. The pH in this step is between 10.5 and 11, optimal pH for enriching the extract with small RNA.

This mixture is then stirred for 1 hour at 50° C. Even if the temperature at this stage can vary from 25° C. to 80° C. and the stirring time from 30 minutes to 1 h, for this species, a temperature of 50° C. for 60 minutes is found to constitute the conditions which make it possible to obtain the best results in terms of enrichment of the final aqueous extract with low molecular weight RNA.

After this step, the mixture is centrifuged for 10 min at 4000 g in order to remove the solid matter.

Then sequential filtrations are carried out through filters of decreasing porosity having sizes between 20 and 50 µm, then 7 and 20 µm, up to 2-4 µm in order to clarify the plant extract.

In this step, the pH is checked, in order to bring it, if necessary, to between 6 and 6.5 and to preserve the small RNA of the extract, which is sensitive to an acidic pH.

The filtrations are continued up to a porosity of 0.3 to 0.5 µm.

In general, an aqueous extract having an amber color is obtained, which titrates at 10 to 30 g/kg of dry weight extract, 0.5 to 5 g/kg of protein fragments, 2 to 15 g/kg of sugars, 100 to 1500 mg/kg of phenolic compounds, and 10 to 100 mg/kg of low molecular weight RNA having a maximum length of 150 nucleotides.

The extract can then be diluted or stored thanks to the addition of a physiologically acceptable solvent such as glycerol at 30%.

In this example, after addition of 30% solvent, an aqueous extract is obtained, which titrates at 15 g/kg of dry weight extract, 2.3 g/kg of protein fragments, 3.0 g/kg of sugars, 200 mg/kg of phenolic compounds, and 35 mg/kg of low molecular weight RNA having a maximum length of 150 nucleotides.

According to a third aspect of the invention, the aqueous extracts enriched with small RNA obtained according to the invention are advantageously used in the preparation of cosmetic compositions comprising, as active anti-aging agent, an effective quantity of such an extract of small RNA according to the invention, and a physiologically acceptable medium.

The expression effective quantity designates the minimum quantity of extract according to the invention which is necessary for obtaining the activity of the extract, in particular the cosmetic activity, and more particularly activity against the signs of skin aging or for improving the hydration of the skin, without this quantity being toxic.

Advantageously, the extract of small RNA according to the invention is used in its diluted form, with a dry weight between 5 and 35 g/kg.

Advantageously, the extract of small RNA according to the invention is present in the composition at a concentration of 0.1 to 5%, preferably at a concentration of 1 to 5% by weight with respect to the total weight of the composition.

Physiologically acceptable medium designates a vehicle suitable for being brought in contact with the external layers of the skin or the mucous membranes, without toxicity, irritation, similar undue allergic response and the like or intolerance reaction, and proportioned for a reasonable advantage/risk ratio.

The composition which can be used according to the invention can be applied by any appropriate route, notably an oral route, or an external topical route; and the formulation of the compositions will be adapted by the person skilled in the art.

Preferably, the compositions according to the invention are in a form suitable for the application by topical route. These compositions therefore must contain a physiologically acceptable medium, that is to say a medium which is compatible with the skin and appendages without risk of discomfort during their application, and cover all the suitable cosmetic forms.

The expression topical application designates the fact that the aqueous extract enriched with small RNA according to the invention, and more particularly the composition containing the extract, is applied or spread on the surface of the skin or of a mucous membrane.

Skin designates more particularly the facial skin, notably the contour of the eyes and of the mouth, the nose, the forehead, the neck, the hands, as well as the skin of the rest of the body.

The compositions for the implementation of the invention can notably be in the form of an aqueous, water-alcohol or oily solution, an oil-in-water or water-in-oil emulsion or multiple emulsions; they can also be in the form of suspensions, or also powders, suitable for application to the skin, the mucous membranes, the lips and/or the hair.

These compositions can be more or less fluid and they can also be in the form of a cream, a lotion, a milk, a serum, an ointment, a gel, a paste or a foam. They can also be in a solid form, such as, a stick, or they can be applied to the skin in the form of an aerosol.

As a physiologically acceptable medium commonly used in the application field in question, one can mention, for example, adjuvants necessary for the formulation, such as solvents, thickeners, diluents, antioxidants, dyes, sunscreen filters, self-tanning agents, pigments, fillers, preservatives, perfumes, odor absorbers, essential oils, vitamins, essential fatty acids, surfactants, film producing polymers, etc.

In all the cases, the person skilled in the art will ensure that these adjuvants as well as their proportions are selected in such a manner that they are not detrimental to the desired advantageous properties of the composition according to the invention. These adjuvants can, for example, correspond to 0.01 to 20% of the total weight of the composition. When the composition according to the invention is an emulsion, the oily phase can represent 5 to 80% by weight and preferably 5 to 50% by weight with respect to the total weight of the composition. The emulsifiers and co-emulsifiers used in the composition are selected from those conventionally used in the field in question. For example, they can be used in a proportion ranging from 0.3 to 30% by weight with respect to the total weight of the composition.

According to another advantageous embodiment of the invention, the aqueous extract enriched with small RNA according to the invention can be encapsulated or included in a cosmetic vector such as liposomes or any other nanocapsule or microcapsule used in the field of cosmetics or can be adsorbed to powdered organic polymers, mineral supports such as talcs and bentonites.

Advantageously, the composition according to the invention can comprise, in addition to the active agent according to the invention, at least one other active agent which has cosmetic effects similar and/or supplemental to those of the invention. According to the invention, this active agent is defined as an "additional active agent."

For example, the additional active agent(s) can be selected from: the anti-aging agents, skin firming agents, brighteners, hydration agents, draining agents, microcirculation promoting agents, exfoliants, desquamation agents, agents stimulating the extracellular matrix, agents activating the energy metabolism, antibacterial agents, antifungal agents, calming agents, anti-free radical agents, anti-UV agents, anti-acne agents, anti-inflammatories, anesthetics, agents procuring a sensation of heat, agents procuring a sensation of freshness, slimming agents.

Such additional active agents can be selected from the groups comprising:

vitamin A and notably retinoic acid, retinol, retinol proprionate, retinol palmitate;

vitamin B3 and more particularly niacinamide, tocopherol nicotinate;

vitamin B5, vitamin B6, vitamin B12, panthenol;

vitamin C, notably ascorbic acid, ascorbyl glucoside, ascorbyl tetrapalmitate, magnesium and sodium ascorbyl phosphate;

vitamins E, F, H, K, PP, coenzyme Q10;

metalloproteinase inhibitors, or an activator of TIMP;

DHEA, precursors and derivatives thereof;

amino acids such as arginine, ornithine, hydroxyproline, hydroxyproline dipalmitate, palmitoylglycine, hydroxylysine, methionine and derivatives thereof, N-acylated amino acid compounds;

natural or synthetic peptides including di-, tri-, tetra-, penta- and hexapeptides and lipophilic derivatives thereof, isomeric derivatives thereof, and derivatives thereof which are complexed with other species such as a metal ion (for example, copper, zinc, manganese, magnesium, and others). As examples, one can mention the peptides commercially known under the name of MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or the synthetic peptide having the sequence Arg-Gly-Ser-NH$_2$, marketed under the name AlPeptide™ by ASHLAND® the extract of *Artemia salina*, marketed under the name of GP4G™ (FR2817748, ASHLAND®);

plant peptide extracts such as the linseed extracts (Lipigénine™, patent FR2956818, ASHLAND®), extracts of soybean, spelt, grapevine, rapeseed, linseed, rice, corn, pea;

yeast extracts, for example, Dynagen™, (patent FR2951946, ASHLAND®) or Actopontine™ (patent FR2944526, ASHLAND®);

dehydroacetic acid (DHA);

phytosterols of synthetic or natural origin;

salicylic acid and derivatives thereof, alpha- and beta-hydroxy acids, silanols;

amino sugars, glucosamine, D-glucosamine, N-acetyl glucosamine, N-acetyl-D-glucosamine, mannosamine, N-acetyl mannosamine, galactosamine, N-acetyl galactosamine;

extracts of polyphenols, isoflavones, flavonoids, such as the grape extracts, the pine extracts, olive extracts;

lipids such as ceramides or phospholipids, oils of animal origin such as squalene or squalane; plant oils such as sweet almond, copra, *ricinus*, jojoba, olive, rapeseed, peanut, sunflower seed, wheat germ, corn germ, soybean, cotton, alfalfa, poppy, pumpkin, evening primrose, millet, barley, rye, safflower, passion flower, hazelnut, palm, apricot seed, avocado and calendula oils; ethoxylated plant oils, Shea butter;

all UV screens and sunscreens;

cyclic AMP and derivatives thereof, adenylate cyclase enzyme activating agents and phosphodiesterase enzyme inhibiting agents, extract of *Centella asiatica*, asiaticoside and asiatic acid, methyl xanthines, theine, caffeine and derivatives thereof, theophylline, theobromine, forskolin, esculin and esculoside, ACE inhibitors, Val-Trp peptide, neuropeptide Y inhibitors, enkephalin, extract of *Ginkgo biloba*, extract of

*dioscorea*, rutin, yerba mate extract, guarana extract, oligosaccharides, polysaccharides, carnitine, ivy extract, fucus extract, hydrolyzed extract of Prunella vulgaris, hydrolyzed extract of *Celosia cristata*, extract of Anogeissus leiocarpus, extract of *Manihot utilissima* leaves, palmitoylcarnitine, carnosine, taurine, extract of elderberry, algae extracts such as extract of *Palmaria palmata*.

As an illustration, examples of formulations of a cosmetic composition containing an aqueous extract enriched with small RNA having a maximum length of 150 nucleotides obtained according to the invention are mentioned below:

Example 17: Balm for the Contour of the Eyes

| Ingredients(Trademark) | INCI | % w/w |
|---|---|---|
| Phase A | | |
| Purified water | Aqua | Qsp 100 |
| Tetrasodium EDTA | Tetrasodium EDTA | 0.01 |
| Phase B | | |
| RapiThix ™ A-100 polymer | Sodium Polyacrylate | 1.80 |
| Phase C | | |
| Cegesoft VP | Vegetable oil (and) Hydrogenated vegetable oil (and) *Euphorbia Cerifera* (Candelilla) Wax | 3.00 |
| Si-Tec ™ GF 3096 silicone | Dimethicone (and) Dimethiconol | 10.00 |
| Phase D | | |
| DC 9701 Cosmetic Powder | Dimethicone/Vinyl Dimethicone Crosspolymer (and) Silica | 1.00 |
| Phase E | | |
| Optiphen ™ preservative | Phenoxyethanol (and) Caprylyl Glycol | 0.50 |
| Phase F | | |
| Extract according to example 5 | Water/Aqua (and) Glycerin (and) Hydrolyzed *Hibiscus esculentus* extract | 1.00 |
| Zemea ® | Propanediol | 5.00 |
| Timiron Splendid Violet | CI 77891 (Titanium Dioxide) (and) Mica (and) Silica | 1.00 |

Preparation Method:
1. Homogenize phase A in the main container until it is clear;
2. At 25° C., sprinkle in Phase B and homogenize for 10 minutes up to homogeneity;
3. At 25° C., prepare phase C in a separate beaker, mix up to homogeneity. Sprinkle in phase D and thoroughly mix up to homogeneity;
4. At 25° C., add phase C+D to the main container and mix up to homogeneity;
5. At 25° C., add phase E to the main container and mix up to homogeneity;
6. At 25° C., premix phase F, add it to the main container and mix up to homogeneity;
7. Stop at 25° C.

The composition is in the form of a purple pearly cream gel having a pH between 5.70 and 6.20 and a viscosity (DO) of 80,000-130,000 cps (Brookfield RVT/Spindle C/5 RPM/1 minute/25° C.)

Example 18: Rich Cream

| Ingredients(Trademark) | INCI | % w/w |
|---|---|---|
| Phase A | | |
| Purified water | Aqua | Qsp 100 |
| Optiphen ™ Plus preservative | Phenoxyethanol (and) Caprylyl Glycol (and) Sorbic Acid | 1.50 |
| Phase B | | |
| Stabileze ™ QM polymer | PVM/MA Decadiene Crosspolymer | 0.15 |
| Phase C | | |
| ProLipid ™ 141 lamellar gel | Glyceryl Stearate (and) Behenyl Alcohol (and) Palmitic Acid (and) Stearic Acid (and) Lecithin (and) Lauryl Alcohol (and) Myristyl Alcohol (and) Cetyl Alcohol | 5.00 |
| Ceraphyl ™ 494 ester | Isocetyl Stearate | 4.00 |
| Ceraphyl ™ SLK ester | Isodecyl Neopentanoate | 4.00 |
| DC 580 Wax | Stearoxytrimethylsilane (and) Stearyl Alcohol | 2.00 |
| Emulsynt ™ GDL ester | Glyceryl Dilaurate | 3.00 |
| Phase D | | |
| Gransil DM-5 | Dimethicone (and) | 3.00 |
| Phase E | | |
| Sodium hydroxide | Sodium Hydroxide | 0.04 |
| Purified water | Aqua | 0.50 |
| Phase F | | |
| PF Precious wood | Perfume/Fragrance | 0.30 |
| Unipure* Red LC 381 ADT-C | CI 77491 (Iron oxides) (and) Isopropyl Titanium Triisostearate (and) Bis-Hydroxyethoxypropyl Dimethicone (and) PEG-2-Soyamine (and) Isophorone | 0.03 |
| Phase G | | |
| Extract according to example 3 | Water/Aqua (and) Glycerin (and) *Lens esculenta* seed | 3.00 |
| Ronaflair Balance Gold | CI 77891 (Titanium Dioxide) (and) Mica (and) Tin Oxide | 0.30 |
| Covabead Velvet 10 | Polymethyl Methacrylate | 1.00 |
| Ronaflair Balance Red | CI 77891 (Titanium Dioxide) (and) Mica (and) Tin Oxide | 1.20 |
| Phase H | | |
| Purified water | Aqua | 15.00 |
| Natrosol ™ Plus 330 CS | Cetyl Hydroxyethylcellulose | 0.50 |

Preparation Method:
1. Homogenize phase A in the main container and start heating at 75-80° C.;
2. At 30° C., sprinkle in phase B and homogenize while heating;
3. In a separate beaker, prepare phase C, heat at 75-80° C. up to homogeneity;
4. At 75° C., add phase C to the main container and homogenize for 10 minutes;
5. Allow the temperature to cool and add phase D at 65° C. Thoroughly mix to homogenize for 10 minutes;
6. Premix phase E before adding it to the main container;
7. Add phase E at 60° C. Thoroughly mix to homogenize for 10 minutes;
8. At 35° C., premix phase F before adding it and thoroughly mix;

9. Premix phase G before adding it to the main container;
10. Add phase G at 35° C. Thoroughly mix to homogenize;
11. In a separate beaker, prepare phase H: sprinkle Natrosol™ into the water at ambient temperature and homogenize the whole preparation while heating at 60° C.;
12. Add phase H at 30° C. Thoroughly mix to homogenize;
13. Stop at 25° C.

The composition is thus in the form of a pink buttery cream having a pH between 4.90 and 5.40 and a viscosity (DO) of 160,000-210,000 cps (Brookfield RVT/Spindle D/5 RPM/1 minute/25° C.)

Example 19: Face Serum

| Ingredients (Trademark) | INCI | % w/w |
|---|---|---|
| Phase A | | |
| Purified water | Aqua | Qsp 100 |
| Propylene glycol | Propylene Glycol | 35.10 |
| SD Alcohol 40B Absolute | Alcohol | 10.00 |
| Butylene glycol | Butylene Glycol | 5.00 |
| Disodium EDTA | Disodium EDTA | 0.10 |
| Phase B | | |
| Flexithix™ polymer | PVP | 2.00 |
| Phase C | | |
| Xanthan gum | Xanthan Gum | 0.25 |
| Phase D | | |
| Rapithix™ A-60 polymer | Sodium Polyacrylate (and) Hydrogenated Polydecene (and) | 1.00 |
| Rokonsal™/LiquaPar™ MEP preservative | Phenoxyethanol (and) Methylparaben (and) Ethylparaben (and) | 0.70 |
| Phase E | | |
| Extract according to example 7 | Water/Aqua (and) Glycerin (and) | 5.00 |
| Phase F | | |
| Cyclopentasiloxane | Cyclopentasiloxane | 6.00 |
| DM 350 | Dimethicone | 3.00 |
| Gransil* DMCM-5 | Dimethicone (and) Cyclopentasiloxane (and) Polysilicone-11 | 1.50 |
| KSP* 100 | Vinyl Dimethicone/Methicone Silsesquioxane | 1.00 |
| Phase G | | |
| Unicert* Yellow 08006-J (Sol. 0.1%) | Water/Aqua (and) CI 15985 (Yellow 6) | 0.60 |

Preparation Method:
1. In a beaker at ambient temperature, weigh the ingredients of phase A and mix. Sprinkle phase B and homogenize;
2. At ambient temperature, sprinkle in phase C and continue to homogenize the whole preparation;
3. At ambient temperature, add phase D to phase ABC and continue to homogenize;
4. At ambient temperature, add phase E and homogenize;
5. At ambient temperature, add phase F and homogenize the whole preparation;
6. At ambient temperature, add phase G and mix up to homogeneity;
7. Stop at 25° C.

The composition is thus in the form of a smooth, translucent, cream yellow gel having a pH between 6.30 and 7.10 and a viscosity (DO) of 10,000-15,000 cps (Brookfield RVT/Spindle B/5 RPM/1 minute/25° C.)

Example 20: Anti-Aging Mask

| Ingredients (Trade Name) | INCI | % w/w |
|---|---|---|
| Phase A | | |
| Purified water | Aqua | Qsp 100 |
| Tetrasodium EDTA | Tetrasodium EDTA | |
| Phase B | | |
| N-Hance™ HP40S guar | Hydroxypropyl Guar | 0.10 |
| Phase C | | |
| Lubrajel™ DV Free hydrogel | Glycerin (and) Glyceryl Acrylate/Acrylic Acid Copolymer | 6.00 |
| Phase D | | |
| Si-Tec™ GF 3096 silicone | Dimethicone (and) Dimethiconol | 12.00 |
| RapiThix™ A-60 polymer | Sodium Polyacrylate (and) Hydrogenated Polydecene (and) Trideceth-6 | 2.40 |
| Phase E | | |
| Optiphen™ Plus preservative | Phenoxyethanol (and) Caprylyl Glycol (and) Sorbic Acid | 1.50 |
| Phase F | | |
| Surfin* 96 | Alcohol Denat. | 3.50 |
| PF Cucumber & Aloe | Perfume/Fragrance | 0.50 |
| Phase G | | |
| Extract according to example 10 | Water/Aqua (and) Glycerin (and) Hydrolyzed *Cucurbita pepo* seedcake extract | 1.00 |
| Achromaxyl™ ISR biofunctional | Water/Aqua (and) Glycerin (and) Hydrolyzed *Brassica Napus* Seedcake Extract | 3.00 |
| Xirona Carribean Blue | Mica (and) CI 77891 (Titanium Dioxide) (and) Silica (and) Tin Oxide | 1.00 |

Preparation Method
1. At 25° C., homogenize phase A in the main container;
2. At 25° C., sprinkle in phase B and thoroughly mix up to homogeneity;
3. At 25° C., add phase C and thoroughly mix up to homogeneity;
4. Premix phase D in a separate beaker and add to the main container at 25° C.;
5. At 25° C., add phase E to the main container and thoroughly mix;
6. Premix phase F and add it slowly. Thoroughly mix up to homogeneity;
7. Premix phase G in a separate beaker and add to the main container up to homogeneity;
8. Stop at 25° C.

The composition is thus in the form of a gel cream with scintillating green effects having a pH between 5.30 and 5.80 and a viscosity (DO) of 70,000-100,000 cps (Brookfield RVT/Spindle C/5 RPM/1 minute/25° C.)

Example 21: Serum

| Ingredients (Trade Name) | INCI | % w/w |
|---|---|---|
| *Phase A* | | |
| Demineralized water | Aqua | 87.40 |
| Sodium hyaluronate | Sodium Hyaluronate | 0.20 |
| RapiThix ™ A-60 polymer | Sodium Polyacrylate (and) Hydrogenated Polydecene (and) Trideceth-6 | 0.40 |
| Lubrajel ™ DV hydrogel | Glycerin (and) Glyceryl Acrylate/Acrylic Acid Copolymer (and) Propylene Glycol | 6.00 |
| Lubrajel ™ Oil hydrogel | Glycerin (and) Glyceryl Acrylate/Acrylic Acid Copolymer (and) Propylene Glycol (and) PVM/MA Copolymer | 1.00 |
| Wacker-Belsil* DM 100 | Dimethicone | 2.00 |
| Cyclopentasiloxane NF | Cyclopentasiloxane | 0.50 |
| Extract according to example 11 | Water/Aqua (and) Glycerin (and) *Chenopodium quinoa* seed extract | 1.00 |
| Optiphen ™ preservative | Phenoxyethanol (and) Caprylyl Glycol | 1.50 |

Preparation Method:

1. Add water to the main container and start mixing with a hi-lo helix blade;
2. Add the rest of the ingredients, one after the other, while mixing between each addition.

The composition is thus in the form of a smooth semi-opaque serum having a pH between 5.75 and 6.25 and a viscosity (DO) of 1100-1400 cps (Brookfield RVT/spindle 3/20 rpm/25° C./1 minute).

According to a fourth aspect, the invention relates to the cosmetic use of the composition according to the invention for combating the signs of skin aging.

The expression "signs of skin aging" is understood to mean any modifications of the external appearance of the skin which are due to aging, such as, for example, wrinkles and small wrinkles, cracks, pouches under the eyes, dark circles under the eyes, shriveling, loss of elasticity, firmness and/or tone of the skin, but also any internal modifications of the skin which are not systematically reflected in a modified external appearance, such as, for example, thinning of the skin or any internal degradations of the skin consecutive to environmental stresses such as pollution and UV radiation.

The study of the expression of the collagens of the skin is one means of assessing the anti-aging effect of the invention. In fact, collagen synthesized by the fibroblasts of the skin has an important biological role. It is responsible for the cohesion of the tissues such as the skin, and it confers properties of resistance and flexibility to the skin.

The invention also relates to the cosmetic use of the composition according to the invention for improving the hydration of the skin.

Improving the hydration of the skin is understood to mean any improvements of the modifications of the external appearance of the skin which are due to dehydration such as, for example, dryness, tightness and discomfort.

The study of the expression of hyaluronic acid and of the enzyme involved in the synthesis of hyaluronic acid is one means of assessing the hydrating effect of the invention. In fact, hyaluronic acid is a major component of the extracellular matrix of the dermis and also present in the epidermis, and is involved in the skin hydration.

In this regard, the invention is illustrated below by the different results of tests performed.

To this effect, results that are similar (not represented) to those represented in examples 22 to 25 below were obtained with other aqueous extracts enriched with small RNA having a maximum length of 150 nucleotides according to the invention, obtained from plant material and more particularly from *Chenopodium quinoa* (quinoa), *Lens esculenta* (lentil), *Oryza sativa* (rice germ), or *Cucurbita pepo* (squash).

Example 22: Evaluation of the Effects of the Extracts of Okra (*Hibiscus esculentus*) According to Examples 5, 6 and 9 on the Extracellular Matrix of the Dermis by the Study of Collagens I and III The purpose of this study is to compare the effects of three extracts of okra (*Hibiscus esculentus*) on the extracellular matrix of the dermis. The first extract enriched with low molecular weight RNA obtained according to example 5, the second extract obtained according to example 6 (absence of treatment with EDTA), and the last extract obtained after precipitation according to example 9.

The purpose of this study is to evaluate the effects of these three extracts of *Hibiscus esculentus* on the expression of the collagen I and III proteins involved in the structure of the extracellular matrix. Collagen is very important for maintaining the elasticity and the firmness of the skin.

Protocol:

Biopsies of human skin having a diameter of 6 mm are maintained in culture ex vivo in the presence of a specific medium (DMEM 1 g/L, HAMF12, SVF and antibiotics) on inserts deposited in 6-well plates. The biopsies are cultured for 48 h and receive 2 applications per day of an extract of okra (*Hibiscus esculentus*) according to examples 5, 6 and 9 diluted to 1/100 or to 3/100 in PBS, or at the final concentration of 1% and 3% volume/volume, respectively. The control condition is brought about with the aid of PBS 1×. The applications are made in the form of a drop of approximately 20 µL deposited on the surface of the biopsy. The biopsies are then fixed in formaldehyde, and then included in paraffin. Skin sections having a thickness of 4 µm are then prepared. The labeling of collagens I and III is carried out after unmasking the specific sites by microwave incubation, followed by a treatment with trypsin. The immunolabeling is carried out with the aid of a collagen I specific rabbit polyclonal antibody (Rockland, Ref. 600-401-103-0.5), of a collagen III specific rabbit polyclonal antibody (Rockland, Ref. 600-401-105-0,5), then of a anti-rabbit secondary antibody coupled with a fluorochrome (Invitrogen, Ref. A21206). The biopsies are then examined under the Epi-fluorescence microscope (Zeiss Axiovert 200M microscope). A quantification of the fluorescence with the aid of the software Volocity® image analysis software (PerkinElmer, Inc.) was carried out based on the photographs obtained.

Results:

The treatments with the extract of okra (*Hibiscus esculentus*) enriched with small RNA obtained according to example 5 at 1% and 3% make it possible to observe a significant increase in the expression of collagens I and III in comparison to the control condition treated with PBS 1× and compared to the treatments with the extracts of okra (*Hibiscus esculentus*) obtained according to examples 6 (without EDTA treatment) and 9 (obtained after precipitation), for the ex vivo study.

|  | Expression of collagen I (%) | Expression of collagen III (%) |
|---|---|---|
| Not treated | 100 | 100 |
| Extract of *Hibiscus esculentus* according to example 5 at 1% | 116.3 | 136.2 |
| Extract of *Hibiscus esculentus* according to example 5 at 3% | 112.7 | 179.2 |
| Extract of *Hibiscus esculentus* according to example 6 at 1% | 101.6 | 115.6 |
| Extract of *Hibiscus esculentus* according to example 6 at 3% | 102.9 | 100 |
| Extract of *Hibiscus esculentus* according to example 9 at 1% | 114.5 | 118.9 |
| Extract of *Hibiscus esculentus* according to example 9 at 3% | 100.5 | 116.8 |

Conclusions:

The extract of okra (*Hibiscus esculentus*) enriched with small RNA (example 5) at 1 and 3% stimulates the expression of collagens I and III more in human ex vivo skin compared to the two extracts of *Hibiscus esculentus* which are not enriched with small RNA (examples 6 and 9) at 1% and 3%.

Example 23: Evaluation of the Effects of the Extracts of Baobab (*Adansiona digitata*) According to Examples 7, 8 and 9 on the Extracellular Matrix of the Dermis by the Study of Collagens I and III The purpose of this study is to compare the effects of three extracts of baobab (*Adansiona digitata*) on the extracellular matrix of the dermis. The first extract enriched with low molecular weight RNA obtained according to example 7, the second extract obtained according to example 8 (without EDTA treatment), and the last extract obtained after precipitation according to example 9.

The purpose of this study is to evaluate the effects of these three extracts of baobab (*Adansiona digitata*) on the expression of the collagen I and III proteins involved in the structure of the extracellular matrix. Collagen is very important for maintaining the elasticity and the firmness of the skin.

Protocol:

Biopsies of human skin having a diameter of 6 mm are maintained in culture ex vivo in the presence of a specific medium (DMEM 1 g/L, HAMF12, SVF and antibiotics) on inserts deposited in 6-well plates. The biopsies are cultured for 48 h and receive 2 applications per day of an extract of baobab (*Adansiona digitata*) according to examples 7, 8 and 9 diluted to 1/100 and to 3/100 in PBS or at the final concentration of 1% and of 3% volume/volume, respectively. The control condition is brought about with the aid of PBS 1×. The applications are carried out in the form of a drop of approximately 20 µL deposited on the surface of the biopsy. The biopsies are then fixed in formaldehyde and then included in paraffin. Skin sections having a thickness of 4 µm are then prepared. The labeling of collagens I and III is carried out after unmasking of the specific sites by microwave incubation, followed by a treatment with trypsin. The immunolabeling is carried out with the aid of a collagen I specific rabbit polyclonal antibody (Rockland, Ref. 600-401-103-0.5), a collagen III specific rabbit polyclonal antibody (Rockland, Ref 600-401-105-0.5), then an anti-rabbit secondary antibody coupled with a fluorochrome (Invitrogen, Ref. A21206). The biopsies are then examined under the Epi-fluorescence microscope (Zeiss Axiovert 200M microscope). A quantification of the fluorescence, with the aid of the software Volocity® image analysis software (PerkinElmer, Inc.), was carried out based on the photographs obtained.

Results:

The treatment with the extract of baobab (*Adansiona digitata*) enriched with small RNA obtained according to example 7 at 1% makes it possible to observe a significant increase in the expression of collagen I compared to the control condition treated with PBS 1× and compared to the treatments at 1% with the extracts of *Adansiona digitata* obtained according to examples 8 (without EDTA treatment) and 9 (obtained after precipitation), for the ex vivo study.

The treatment with the extract of baobab (*Adansiona digitata*) enriched with small RNA obtained according to example 7 at 3% makes it possible to observe a significant increase in the expression of collagens I and III compared to the control condition treated with PBS 1× and compared to the treatments at 3% with the extracts of baobab (*Adansiona digitata*) obtained according to examples 8 (without EDTA treatment) and 9 (obtained after precipitation), for the ex vivo study.

|  | Expression of collagen I (%) | Expression of collagen III (%) |
|---|---|---|
| Not treated | 100 | 100 |
| Extract of *Adansiona digitata* according to example 7 at 1% | 130 | — |
| Extract of *Adansiona digitata* according to example 7 at 3% | 134.4 | 149 |
| Extract of *Adansiona digitata* according to example 8 at 1% | 103.2 | — |
| Extract of *Adansiona digitata* according to example 8 at 3% | 107.2 | 107.4 |
| Extract of *Adansiona digitata* according to example 9 at 1% | 100 | — |
| Extract of *Adansiona digitata* according to example 9 at 3% | 100 | 110.8 |

Conclusions:

The extract of baobab (*Adansiona digitata*) enriched with small RNA (example 7) at 1% stimulates the expression of collagen I more in human skin ex vivo compared to the extracts of *Adansiona digitata* which are not enriched with small RNA (examples 8 and 9) at 1%.

The extract of baobab (*Adansiona digitata*) enriched with small RNA (example 7) at 3% stimulates the expression of collagens I and III more in human skin ex vivo compared to the extracts of *Adansiona digitata* which are not enriched with small RNA (examples 8 and 9) at 3%.

Example 24: Evaluation of the Effects of the Extracts of Baobab (*Adansiona digitata*) According to Examples 7, 8 and 9 on the Synthesis of Hyaluronic Acid of the Dermis by the Study of Hyaluronane Synthase 2 (HAS2)

The purpose of this study is to compare the effects of three extracts of baobab (*Adansiona digitata*) on the expression of HAS2, enzyme involved in the synthesis of hyaluronic acid. The first extract enriched with low molecular weight RNA is obtained according to example 7, the second extract obtained according to example 8 (without EDTA treatment), and the last extract obtained after precipitation according to example 9.

Hyaluronic acid is a major component of the extracellular matrix of the dermis, involved in the hydration of the skin.

During aging, its renewal is disturbed, as is the expression of its HAS2 synthesis enzyme (Rock et al., 2014).

Protocol:

Human fibroblasts are cultured in a specific medium and maintained in culture for long-term treatment (for more than 32 passages). At each passage, some of the cells are frozen. Then two opposite passages are selected: passage 8 (young passage) and passage 32 (senescent passage). After thawing, the senescent or non-senescent fibroblasts are treated with the extracts of baobab (*Adansiona digitata*) according to examples 7, 8 and 9 diluted to 1/100 in the culture medium or at the final concentration of 1% volume/volume, for 48 hours (2 applications per day). The evaluation of the expression of HAS2 on the senescent or non-senescent fibroblasts, treated or not treated with the three extracts of *Adansiona digitata* according to examples 7, 8 and 9 at 1%, is observed by immunolabeling.

To achieve this, the cells are rinsed and fixed with cold methanol for 5 minutes. After saturation of the nonspecific sites with bovine serum albumin at 1% for 15 min, the cells are incubated with a solution of HAS2 specific murine monoclonal antibodies (Thermo Fisher, Ref. MAS-17087), then with a solution of anti-mouse secondary antibodies coupled with a fluorochrome (Invitrogen, Ref. A21202). The cells are then examined under the Epi-fluorescence microscope (Zeiss Axiovert 200M microscope). A quantification of the fluorescence, with the aid of the software Volocity® image analysis software (PerkinElmer, Inc.) was carried out based on the photographs obtained.

Results:

As illustrated in FIG. 4A, the treatment with the extract of baobab (*Adansiona digitata*) enriched with small RNA having a maximum length of 150 nucleotides, obtained according to example 7, at 1% on fibroblasts of passage 8 (passage considered young) makes it possible to observe a significant increase in the expression of HAS2 in comparison to the untreated condition and also in comparison to the treatments at 1% with the extracts of *Adansiona digitata* obtained according to examples 8 (without EDTA treatment) and 9 (obtained after precipitation).

In addition, in agreement with the literature, as illustrated in FIG. 4B, a significant decrease in the expression of HAS2 is observed between the passage 8 fibroblasts (P8) and the passage 32 fibroblasts (P32) (senescent).

The treatment with the extract of baobab (*Adansiona digitata*) enriched with small RNA according to the invention obtained according to example 7 at 1% (volume/volume) on senescent fibroblasts makes it possible to observe maintenance of the HAS2 expression. This maintenance is not observed on the cells treated with the extracts of *Adansiona digitata* obtained according to examples 8 (without EDTA treatment) and 9 (obtained after precipitation), respectively.

Conclusion:

The extract of baobab (*Adansiona digitata*) enriched with small RNA having a maximum length of 150 nucleotides (example 7) at 1% stimulates the expression of HAS2 more in fibroblasts compared to the untreated condition and compared to the extracts of *Adansiona digitata* obtained according to examples (without EDTA treatment) and 9 (obtained after precipitation).

In addition, on senescent fibroblasts, the extract of baobab (*Adansiona digitata*) enriched with small RNA according to the invention (example 7) at 1% makes it possible to maintain the level of expression of HAS2 observed on the non-senescent fibroblasts. The other extracts of *Adansiona digitata* not enriched with small RNA (examples 8 and 9) at 1% do not allow this maintenance.

Example 25: Evaluation of the Effects of the Extract of Okra (*Hibiscus esculentus*) According to Example 5 and of the Extract of Baobab (*Adansiona digitata*) According to Example 7 on the Level of Expression of Hyaluronic Acid The purpose of this study is to visualize the effect of the extracts of okra (*Hibiscus esculentus*) and of baobab (*Adansiona digitata*) obtained respectively according to examples 5 and 7, extracts which are enriched with low molecular weight RNA having a maximum length of 150 nucleotides, on the expression of hyaluronic acid by labeling.

Hyaluronic acid is a major component of the extracellular matrix of the dermis and is involved in the hydration of the skin.

Protocol:

Human skin biopsies having a diameter of 6 mm are maintained in culture ex vivo in the presence of a specific medium (DMEM 1 g/L, HAMF12, SVF and antibiotics) on inserts deposited in 6-well plates. The biopsies are cultured for 48 h and receive 2 applications per day of the extract of okra (*Hibiscus esculentus*) or of the extract of baobab (*Adansiona digitata*) according to examples 5 and 7 (respectively) diluted at 1% (volume/volume) in PBS or PBS 1× for the control condition. The applications are carried out in the form of a drop of approximately 20 µL deposited on the surface of the biopsy. The biopsies are then fixed in formaldehyde and then included in paraffin. Skin sections having a thickness of 4 µm are then prepared. The sections are incubated in the presence of a hyaluronic acid specific biotonylated protein (Coger, ref: 400-763-1A) and then in the presence of streptavidin coupled with a fluorochrome (Invitrogen, Ref: S32354). The biopsies are then examined under the Epi-fluorescence microscope (Zeiss Axiovert 200M microscope). A quantification of the fluorescence, with the aid of the software Volocity® image analysis software (PerkinElmer, Inc.), was carried out based on the photographs obtained.

Results:

The treatment with the extract of okra (*Hibiscus esculentus*) or the extract of baobab (*Adansiona digitata*) enriched with small RNA, which are obtained according to examples 5 and 7, respectively, at 1% makes it possible to observe a significant increase in the expression of hyaluronic acid in the epidermis or in the dermis compared to the control condition treated with PBS 1×.

| Expression of hyaluronic acid | In the epidermis (%) | In the dermis (%) |
|---|---|---|
| Not treated | 100 | 100 |
| Extract of *Hibiscus esculentus* according to example 5 at 1% | 156 | 127 |
| Extract of *Adansiona digitata* according to example 7 at 1% | 159 | 124 |

Conclusion:

The extract of okra (*Hibiscus esculentus*) and the extract of baobab (*Adansiona digitata*) enriched with small RNA having a maximum length of 150 nucleotides (according to examples 5 and 7) at 1% stimulate the expression of hyaluronic acid in human skin ex vivo in comparison to the control condition treated with PBS 1×.

Of course, the invention is not limited to the embodiments and the examples presented above, and the person skilled in the art, thanks to routine operations, may be led to implement other embodiments which have not been described explicitly and which are covered by the broad scope of the invention.

The invention claimed is:

1. An aqueous extract of plant material, enriched with small RNA having a maximum length of 150 nucleotides, wherein the extract comprises, by weight relative to the total weight of the extract, 5-60 g/kg of dry extract and 10-1000 mg/kg of small RNAs having a maximum length of 150 nucleotides, 0.5 to 30 g/kg of protein fragments and 0.5 to 50 g/kg of sugars, and comprises no DNA.

2. The extract according to claim 1, wherein the extract is diluted in a solvent and comprises, by weight relative to the total weight of the extract, 5-35 g/kg of dry extract, 0.5-20 g/kg of protein fragments, 0.5-30 g/kg of sugars, and 10-500 mg/kg of small RNA having a maximum length of 150 nucleotides.

3. A composition comprising an effective quantity of the extract of claim 1, as an anti-aging active agent, and a physiologically acceptable medium.

4. The composition according to claim 3, wherein the extract is present at a concentration between 1 and 5% by weight of the total weight of the composition.

5. The composition according to claim 3, wherein the composition is formulated for being applied topically to the skin.

* * * * *